(12) United States Patent
Thorwart et al.

(10) Patent No.: US 7,160,903 B2
(45) Date of Patent: Jan. 9, 2007

(54) SULFONYLAMINOCARBOXYLIC ACIDS

(75) Inventors: Werner Thorwart, Hochheim (DE);
Wilfried Schwab, Wiesbaden (DE);
Manfred Schudok, Eppstein/Ts. (DE);
Burkhard Haase, Hofheim (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 10/170,870

(22) Filed: Jun. 13, 2002

(65) Prior Publication Data

US 2003/0087945 A1 May 8, 2003

Related U.S. Application Data

(62) Division of application No. 09/074,693, filed on May 8, 1998, now Pat. No. 6,451,824.

(30) Foreign Application Priority Data

May 9, 1997 (DE) ............................ 197 19 921

(51) Int. Cl.
*A61K 31/381* (2006.01)
*C07D 409/04* (2006.01)
*C07C 311/19* (2006.01)

(52) U.S. Cl. .................. 514/336; 514/378; 546/280.4; 548/247

(58) Field of Classification Search ............. 546/280.4; 548/247; 514/336, 378
See application file for complete search history.

(56) References Cited

U.S. PATENT DOCUMENTS

| | | | | |
|---|---|---|---|---|
| 5,756,545 | A | 5/1998 | O'Brien et al. | 514/562 |
| 6,150,394 | A | 11/2000 | Watanabe et al. | 514/415 |
| 6,159,995 | A | 12/2000 | Thorwart et al. | 514/365 |
| 6,207,698 | B1 * | 3/2001 | Wantanabe et al. | 514/414 |
| 6,235,768 | B1 * | 5/2001 | Wantanabe et al. | 514/414 |

FOREIGN PATENT DOCUMENTS

| | | | |
|---|---|---|---|
| EP | 0 305 947 | B1 | 3/1989 |
| EP | 0 468 231 | B1 | 1/1992 |
| EP | 0 606 046 | B1 | 7/1994 |
| EP | 0 757 037 | A2 | 2/1997 |
| GB | 2263109 | * | 7/1993 |
| WO | WO 95/35276 | | 12/1995 |
| WO | WO 96/00214 | | 1/1996 |
| WO | WO 96/27583 | | 9/1996 |
| WO | WO 96/33172 | | 10/1996 |
| WO | WO 97/19068 | | 5/1997 |
| WO | WO 97/27174 | | 7/1997 |

OTHER PUBLICATIONS

Lechan et al., Endocrinology, Editorial: Hypotharlmic Melanocortin Signalling in Cachexia, 142(8):3288-3291, 2001.*
Avgeropoulos et al., New Treatment Strategies for Malignant Gliomas, The Oncologist, 4:209-224, 1999.*
Simone, Oncology: Introduction, Cecil Textbook of Medicine, 20th Edition, vol. 1, pp. 1004-1010, 1996.*
Catterall et al., Drugs in development: bisphosphonates and metalloproteinase inhibitors, Arthritis Research and Therapy, vol. 5, No. 1, pp. 12-24, 2003.*
Visse et al., Matrix Metalloproteinases and Tissue Inhibitors of Metalloproteinases, Circulation Research, 92:827-839, 2003.*
Sonis, The Pathology of Mucositis, Nat Rev Cancer, 4(4):277-284, 2004.*
Armstrong et al., PubMed Abstract (J Am Podiatr Med Assoc. 92(1):12-8), Jan. 2002.*
Morris et al., Sequential Steps in Hematogenous Metastasis of Cancer Cells Studied by in vivo Videomicroscopy, Invasion Metastasis, 17:281-296, 1997.*
Chambers et al., Changing views of the role of Matrix Metalloproteinases in Metastasis, Journal of the National Cancer Institute, vol. 89, No. 17, Sep. 1997.*
Rasmussen et al., Matrix Metalloproteinase Inhibition as a novel anticancer strategy, Pharmacol. Ther., vol. 75, No. 1, pp. 69-75, 1997.*
Bassin, Jatinder P. et al., "Chlorosulfonation of Some Polynuclear Heterocyclic Compounds," *Phosporus, Sulfur, and Silicon*, vol. 72, pp. 157-170 (1992).
Fosang, Amanda J. et al., "Aggrecan Is Degraded by Matrix Metalloproteinases in Human Arthritis: Evidence that Matrix Metalloproteinase and Aggecanase Activities Can Be Independent," *J. Clin. Invest.*, vol. 98, No. 10, pp. 2292-2299 (Nov. 1996).
Roemmele, Renee C. and Rapoport, Henry, "Removal of N-Arylsulfonyl Groups from Hydroxy α-Amino Acids," *J. Org. Chem.*, vol. 53, pp. 2367-2371 (1988).
Suter, C. M., "Studies in the Diphenyl Ether Series. II. Preparation and Structure of Some Sulfonic Acids and Related Derivatives," *J. Am. Chem. Soc.*, vol. 53, pp. 1112-1116 (1931).
Want, Su-Sun, "p-Alkoxybenzyl Alcohol Resin and p-Alkoxybenzyloxycarbonylhydrazide Resin for Solid Phase Synthesis of Protected Peptide Fragments," *J. Am. Chem. Soc.*, vol. 95, No. 4, pp. 1328-1333 (Feb. 21, 1973).
Ye, Qi-Zhuang et al., "Purification and Characterization of the Human Stromelysin Catalytic Domain Expressed in *Escherichia coli*," *J. Biochemistry*, vol. 31, pp. 11231-11235 (1992).

* cited by examiner

*Primary Examiner*—Deepak Rao
(74) *Attorney, Agent, or Firm*—Ronald G. Ort

(57) ABSTRACT

Compounds of formula (I)

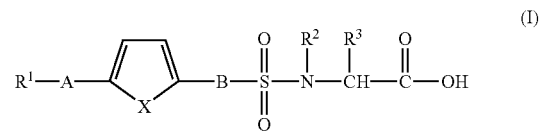

are suitable for the production of pharmaceuticals for the prophylaxis and therapy of disorders in the course of which an increased activity of matrix-degrading metalloproteinases is involved.

2 Claims, No Drawings

SULFONYLAMINOCARBOXYLIC ACIDS

The present application is a divisional application of U.S. application Ser. No. 09/074,693, filed May 8, 1998 now U.S. Pat. No. 6,451,824, the disclosure of which is incorporated in its entirety herein by reference.

The invention relates to novel sulfonylaminocarboxylic acids, processes for their preparation and use thereof as pharmaceuticals for the treatment of connective tissue disorders.

Patent applications EP 0 606 046, WO 95/35276 and WO 96/27583 describe arylsulfonamidohydroxamic acids and their action as matrix metalloproteinase inhibitors. Specific arylsulfonamidocarboxylic acids are used as intermediates for the preparation of thrombin inhibitors (EP 0 468 231) and aldose reductase inhibitors (EP 0 305 947). Patent application EP 0 757 037 also describes the action of sulfonylaminocarboxylic acid derivatives as metalloproteinase inhibitors. It is also known to those skilled in the art that the arylsulfonyl group has proven usefulness as an effective protective group of the amino function of α-aminocarboxylic acids (R. Roemmele, H. Rapoport, *J. Org. Chem.* 53 (1988) 2367–2371).

In the attempt to find efficacious compounds for the treatment of connective tissue disorders, it has now been found that the sulfonylaminocarboxylic acids according to the invention are strong inhibitors of matrix metalloproteinases. Particular value is placed here on the inhibition of stromelysin (matrix metalloproteinase 3) and of neutrophil collagenase (MMP-8), since both enzymes are substantially involved, as important constituents of the cartilaginous tissue, in the degradation of the proteoglycans (A. J. Fosang et al., *J. Clin. Invest.* 98 (1996) 2292–2299).

The invention therefore relates to compounds of formula (I)

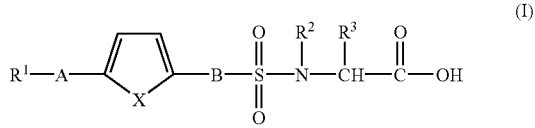

or stereoisomeric forms of the compound of formula (I), or a physiologically tolerable salt of the compound or the stereoisomeric forms of the compound of formula (I), where $R^1$ is
1. phenyl,
2. phenyl, which is mono- or disubstituted by
   2.1. $(C_1-C_6)$-alkyl, which is linear, cyclic, or branched,
   2.2. hydroxyl,
   2.3. $(C_1-C_6)$-alkyl-C(O)—O—,
   2.4. $(C_1-C_6)$-alkyl-O—,
   2.5. $(C_1-C_6)$-alkyl-O—$(C_1-C_4)$-alkyl-O—,
   2.6. halogen,
   2.7. —$CF_3$,
   2.8. —CN,
   2.9. —$NO_2$,
   2.10. HO—C(O)—,
   2.11. $(C_1-C_6)$-alkyl-O—C(O)—,
   2.12. methylenedioxo,
   2.13. $R^4$—($R^5$)N—C(O)—,
   2.14. $R^4$—($R^5$)N—, or
3. a heteroaromatic ring structure as defined below under 3.1. to 3.15., which is unsubstituted, or substituted by the radicals as defined under 2.1 to 2.14.,
   3.1. pyrrole,
   3.2. pyrazole,
   3.3. imidazole,
   3.4. triazole,
   3.5. thiophene,
   3.6. thiazole,
   3.7. oxazole,
   3.8. isoxazole,
   3.9. pyridine,
   3.10. pyrimidine,
   3.11. indole,
   3.12 benzothiophene,
   3.13. benzimidazole,
   3.14. benzoxazole, or
   3.15. benzothiazole;
$R^2$, $R^4$, and $R^5$ are identical or different and each independently are
1. a hydrogen atom,
2. $(C_1-C_6)$-alkyl-,
3. HO—C(O)—$(C_1-C_6)$-alkyl-,
4. phenyl-$(CH_2)_n$—, in which phenyl is unsubstituted, or mono- or disubstituted by the radicals as defined under 2.1. to 2.14., or is substituted by —NH—C(O)—$(C_1-C_3)$-alkyl, and n is the integer zero, 1, or 2, or
5. picolyl, or
6. $R^4$ and $R^5$ together with the ring amino group form a 4- to 7-membered ring, in which one of the carbon atoms is optionally replaced by —O—, —S—, or —NH—, or in which two adjacent carbon atoms of the 4- to 7-membered ring are part of a benzyl radical;
$R^3$ is
1. a hydrogen atom,
2. $(C_1-C_{10})$-alkyl, in which alkyl is unsubstituted, or in which a hydrogen atom of the alkyl radical is replaced by —OH,
3. $(C_2-C_{10})$-alkenyl-, in which alkenyl is linear or branched,
4. $R^2$—O—$(C_1-C_6)$-alkyl-,
5. $R^2$—S(O)$_n$—$(C_1-C_6)$-alkyl-, where n is as defined above,
6. $R^2$—S(O)(=NH)—$(C_1-C_6)$-alkyl-,
7.

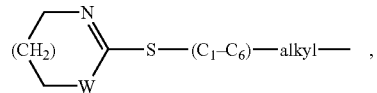

in which n is the integer zero, 1, or 2, and
   W is a nitrogen, oxygen or sulfur atom,
8. phenyl-$(CH_2)_m$—, in which m is the integer zero, 1, 2, 3, 4, 5, or 6, —$(CH_2)_m$— is unsubstituted, or a hydrogen atom of —$(CH_2)_m$— is replaced by —OH, and phenyl is unsubstituted, or mono- or disubstituted by
   8.1. the radicals as defined under 2.1. to 2.14.,
   8.2. —O—$(CH_2)_m$-phenyl, in which phenyl is unsubstituted, or mono- or disubstituted by the radicals as defined under 2.1. to 2.14., and m is the integer zero, 1, 2, 3, 4, 5, or 6, or
   8.3. —C(O)—$(CH_2)_m$-phenyl, in which phenyl is as defined under 8.2.,
9. heteroaryl-$(CH_2)_m$—, in which heteroaryl is as defined under 3.1. to 3.15., m is as defined above, or a hydrogen atom of the —(CH2)$_m$— chain is replaced by —OH, and heteroaryl is unsubstituted, or mono- or disubstituted by
  9.1. the radicals as defined under 2.1. to 2.14.,
  9.2. —CH(O),
  9.3. —SO$_2$-phenyl, in which phenyl is unsubstituted or is as defined under 8.2. or 8.3., or
  9.4. —O—(CH$_2$)$_m$-phenyl,
  10. —(CH$_2$)$_m$—P(O)(OH)—(C$_1$–C$_3$)-alkyl, in which m is as defined above, or
  11. R$^6$—C(O)—(C$_1$–C$_6$)-alkyl-, in which
R$^6$ is
  1. a hydrogen atom,
  2. (C$_1$–C$_6$)-alkyl-, in which alkyl is linear, branched or cyclic,
  3. phenyl, in which phenyl is unsubstituted or substituted as described under 2.1. to 2.14.,
  4. heteroaryl, in which heteroaryl is as defined under 3.1. to 3.15., is unsubstituted, or is substituted by the radicals as described under 2.1. to 2.14., or is substituted by —(C$_1$–C$_4$)-alkyl-COOH,
  5. HO—,
  6. R$^2$O—, in which R$^2$ is as defined above,
  7. is R$^4$—(R$^5$)N—, in which R$^4$ and R$^5$ are as defined above,
  8. heteroaryl-(CH$_2$)$_m$—NH—, in which heteroaryl is as defined under 3.1. to 3.15., or as described under 2.1. to 2.14., and m is as defined above,
  9. R$^4$—(R)N—NH—, in which R$^4$ and R$^5$ are as defined above, or
  10. HO—C(O)—CH(R$^3$)—NH—, in which R$^3$ is as defined above; or
R$^2$ and R$^3$ together form a ring having a ring carboxyl group, composing subformula (II):

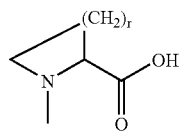

(II)

in which r is the integer zero, 1, 2, or 3, or in which one of the carbon atoms in the ring is replaced by —O—, —S—, or —(R$^7$)N—, in which
R$^7$ is
  1. a hydrogen atom,
  2. (C$_1$–C$_6$)-alkyl,
  3. phenyl, in which phenyl is unsubstituted, or is substituted by the radicals as described under 2.1. to 2.14.,
  4. benzyl, in which benzyl is unsubstituted, or substituted by the radicals as described under 2.1. to 2.14., or
  5. R$^2$N—C(=NH)—, where R$^2$ has the above defined meaning, or the carbon atoms in the ring of subformula (II) are mono- or poly-substituted by (C$_1$–C$_6$)-alkyl-, phenyl-, phenyl-(CH$_2$)$_m$— or HO—;
A is
  a) a covalent bond,
  b) —O—,
  c) —CH=CH—, or
  d) —C≡C—;
B is
  a) —(CH$_2$)$_m$—, in which m has the above defined meaning,
  b) —O—(CH$_2$)$_p$, in which p is the integer from 1, 2, 3, 4, or 5
  c) —CH=CH—; and X is —CH=CH—, an oxygen atom, or a sulfur atom.
A currently preferred compound of formula (I) is where
R$^1$ is
  1. phenyl, or
  2. phenyl, which is monosubstituted by
    2.1. (C$_1$–C$_6$)-alkyl-, in which alkyl is linear, cyclic, or branched,
    2.2. —OH,
    2.3. (C$_1$–C$_6$)-alkyl-C(O)—O—,
    2.4. (C$_1$–C$_6$)-alkyl-O—,
    2.5. (C$_1$–C$_6$)-alkyl-O—(C$_1$–C$_4$)-alkyl-O—,
    2.6. halogen,
    2.7. —CF$_3$, or
    2.8. R$^4$—(R$^5$)N—;
R$^2$, R$^4$, and R$^5$ are identical or different and each independently are
  1. a hydrogen atom, or
  2. (C$_1$–C$_6$)-alkyl-;
R$^3$ is
  1. (C$_1$–C$_{10}$)-alkyl-, in which alkyl is linear, branched, or cyclic, alkyl is unsubstituted, or in which a hydrogen atom of the alkyl radical is replaced by —OH,
  2. R$^2$—S(O)$_n$—(C$_1$–C$_6$)-alkyl-, in which R$^2$ is (C$_1$–C$_6$)-alkyl- or phenyl-(CH$_2$)$_n$, and n is the integer zero or 1,
  3. phenyl-(CH$_2$)$_m$—, in which phenyl is unsubstituted, or mono- or disubstituted by the radicals as described under 2.1. to 2.14., —(CH$_2$)$_m$— is unsubstituted, or a hydrogen atom of —(CH$_2$)$_m$— is replaced by —OH, and m is the integer 1, 2, 3, 4, or 5,
  4. heteroaryl-(CH$_2$)$_m$—, in which heteroaryl is as defined under 3.3., 3.5., 3.6., 3.9., or 3.11., is unsubstituted, or is substituted by the radicals as defined under 2.1. to 2.14., —(CH$_2$)$_m$— is unsubstituted, or a hydrogen atom of the —(CH$_2$)$_m$— chain is replaced by —OH, and m is the integer 1, 2, 3, or 4, or
  5. R$^6$—C(O)—(C$_1$–C$_6$)-alkyl-, in which
R$^6$ is
  1. —OH,
  2. R$^2$O—, in which R$^2$ is defined as above,
  3. R$^4$—(R$^5$)N—, in which R$^4$ and R$^5$ are as defined above, or
  4. R$^4$ and R$^5$ together with the ring amino group form a 5- to 6-membered ring in which one of the carbon atoms is optionally replaced by —O—, —S—, or —NH— or two adjacent carbon atoms of the 5- to 6-membered ring are part of a benzyl radical,
  6. R$^2$ and R$^3$ together form a ring having a ring carboxyl group, of subformula (II), in which n is the integer 1 or 2, and/or one of the carbon atoms in the ring is replaced by —O— or —(R$^7$)N—, in which
R$^7$ is
  1. a hydrogen atom,
  2. (C$_1$–C$_6$)-alkyl,
  3. phenyl, in which phenyl is unsubstituted or substituted as defined under 2.1. to 2.14.,
  4. benzyl, in which benzyl is unsubstituted, or substituted as defined under 2.1. to 2.14., or
  5. R$^2$N—C(=NH)—, in which R$^2$ is as defined above, and/or the carbon atoms in the ring of the subformula (II) are mono-substituted by phenyl or —OH;
A is
  a) a covalent bond or
  b) —O—;

B is
a) —(CH$_2$)$_m$—, in which m is the integer zero, 1, or 2; or
b) —O—(CH$_2$)$_p$—, in which p is an integer 1 or 2; and
X is —CH=CH—.

A compound of formula (I) is particularly preferred where R$^1$ is
1. phenyl or
2. phenyl which is monosubstituted by
   2.1. halogen, in particular chlorine or fluorine, or
   2.2. R$^4$—(R$^5$)N—, where R$^4$ and R$^5$ are identical or different and are
      2.2.1. (C$_1$–C$_3$)-alkyl or
      2.2.2. R$^4$ and R$^5$ together with the ring amino group form a 5- to 6-membered ring in which one of the carbon atoms optionally being replaced by —O— or —N—;

R$^2$ is a hydrogen atom;
R$^3$ is
1. heteroaryl-(CH$_2$)$_m$—, in which heteroaryl is as defined under 3.5, 3.11., or 3.13., and the heteroaryl is unsubstituted, or monosubstituted by the radicals as described under 2.1. to 2.14., and m is the integer 1 or 2, or
2. R$^6$—C(O)—(C$_2$–C$_3$)-alkyl, in which R$^6$ is
1. —OH,
2. R$^2$—O—, in which R$^2$ is as defined above or
3. R$^4$—(R$^5$)N—, in which R$^4$ and R$^5$ are identical or different and are
   3.1. a hydrogen atom,
   3.2. (C$_1$–C$_3$)-alkyl-,
   3.3. phenyl-(CH$_2$)—, where phenyl is unsubstituted, or mono- or disubstituted as defined under 2.1. to 2.14., and n is the integer zero, 1, or 2,
   3.4. R$^4$ and R$^5$ together with the ring amino group form a 5- to 6-membered ring, where one of the carbon atoms is optionally replaced by —O— or —NH—, or form an indoline radical, or
   3.5. HO—C(O)—CH(R$^3$)—NH—, in which R$^3$ is as defined above;

A is a covalent bond;
B is —(CH$_2$)$_o$—, in which o is zero; and
X is —CH=CH—.

The expression "R$^4$ and R$^5$ together with the ring amino group form a 4- to 7-membered ring in which one of the carbon atoms is optionally replaced by —O—, —S—, or —NH—" is understood as meaning radicals which are derived, for example, from azetidine, pyrrole, pyrroline, pyridine, azepine, piperidine, oxazole, isoxazole, imidazole, indoline, pyrazole, thiazole, isothiazole, diazepine, thiomorpholine, pyrimidine or pyrazine. The term "halogen" is understood as meaning fluorine, chlorine, bromine or iodine. The term "alkyl" or "alkenyl" is understood as meaning hydrocarbon radicals whose carbon chains are straight-chain or branched. Cyclic alkyl radicals are, for example, 3- to 6-membered monocyclic systems such as cyclopropyl, cyclobutyl, cyclopentyl or cyclohexyl. Furthermore, the alkenyl radicals can also contain several double bonds. The starting substances of the chemical reactions are known or one of ordinary skill in the art can easily derive and prepare these starting substances by methods known in the literature.

The invention further relates to a process for the preparation of the compound of formula (I) or a stereoisomeric form of the compound of formula (I) or of a physiologically tolerable salt of the compound or the stereoisomeric form of the compound of formula (I), which comprises:

a) reacting an aminocarboxylic acid of formula (III),

(III)

in which R$^2$ and R$^3$ are as defined in formula (I), with a sulfonic acid derivative of formula (IV),

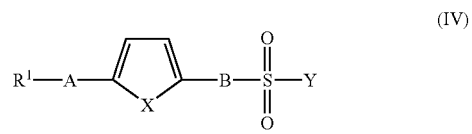

(IV)

in which R$^1$, A and B are as defined in formula (I) and Y is a halogen atom, imidazolyl or —OR$^8$, in which R$^8$ is a hydrogen atom, (C$_1$–C$_6$)-alkyl, phenyl or benzyl, if appropriate substituted, in the presence of a base or optionally of a dehydrating agent to give a compound of formula (I), or b) reacting an aminocarboxylic acid ester of formula (V),

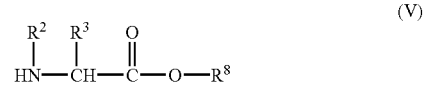

(V)

in which R$^2$, R$^3$ and R$^8$ have the above defined meaning, with a sulfonic acid derivative of formula (IV) under the above defined conditions to give a compound of formula (VI)

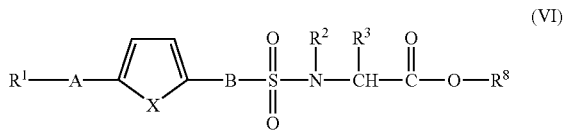

(VI)

and converting the compound of formula (VI) into a compound of formula (I) with removal of the radical R$^8$, preferably in the presence of a base or acid, or c) reacting the compound of formula (VII),

(VII)

where n is the integer zero, 1 or 2, with the aid of a protective group E to give a compound of formula (VIII),

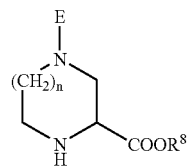
(VIII)

converting the compound of formula (VIII) with a sulfonic acid derivative of formula (IV) under the above defined conditions into a compound of formula (IX)

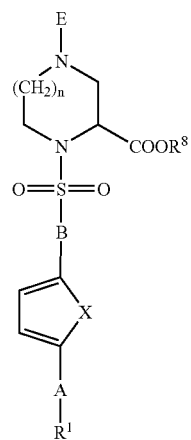
(IX)

and then converting the compound of formula (IX) into the compound of formula (I) by the removal of the protective group E and of the radical $R^8$ with the aid of suitable cleaving reagents.

d) resolving a compound of formula (I), which on account of its chemical structure occurs in enantiomeric forms, prepared by process a), b) or c) into the pure enantiomers by salt formation with enantiomerically pure acids or bases, chromatography on chiral stationary phases or derivatization by means of chiral enantiomerically pure compounds such as amino acids, separation of the diastereomers thus obtained, and removal of the chiral auxiliary groups, or isolating the compound of formula (I) prepared by process a), b), c) or d) either in free form or, in the case of the presence of acidic or basic groups, converting it into physiologically tolerable salts.

Suitable protective groups E used for this purpose are preferably the N-protective groups customary in peptide chemistry, for example, protective groups of the urethane type, benzyloxycarbonyl (Z), t-butoxycarbonyl (Boc), 9-fluorenyloxycarbonyl (Fmoc), allyloxycarbonyl (Aloc) or of the acid amide type, e.g., formyl, acetyl or trifluoroacetyl, and of the alkyl type, e.g., benzyl.

Compounds of formula (III) employed in which $R^2$ is a hydrogen atom and $R^3$ is the characteristic radical of a natural α-amino acid are preferably glycine, alanine, valine, leucine, isoleucine, phenylalanine, tyrosine, tryptophan, serine, threonine, cysteine, methionine, asparagine, glutamine, lysine, histidine, arginine, glutamic acid and aspartic acid. In the case of natural, as well as unnatural, α-amino acids which have a functional group such as amino, hydroxyl, carboxyl, mercapto, guanidyl, imidazolyl or indolyl in the side chain $R^3$, this group can also be protected.

In the case of an imidazole radical in $R^3$, the sulfonic acid derivative of formula (IV) employed for the sulfonamide formation serves, for example, as a protective group of the imidazole nitrogen, which can be removed again, in particular in the presence of bases such as sodium hydroxide solution.

To prepare compounds of formula (I) in which $R^2$ and $R^3$ together form a ring of the substructure II, starting substances of the formula (III) used are, for example, proline, 3- or 4-hydroxyproline, piperidine-2-carboxylic acid, piperazine-2-carboxylic acid and hexahydropyridazine-3-carboxylic acid, it being possible, in particular, for the nitrogen in the 4-position of the piperazine-2-carboxylic acid to be substituted by a protective group Z, for example benzyloxycarbonyl or tert-butyloxycarbonyl as described in process variant c) or by a radical $R^7$.

Starting materials used for the preparation of the sulfonic acid derivatives of formula (IV) are preferably sulfonic acids or their salts of formula (X), for example

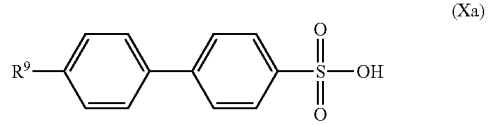
(Xa)

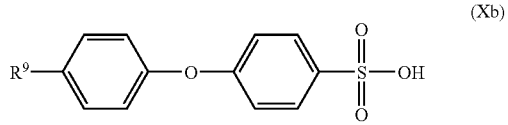
(Xb)

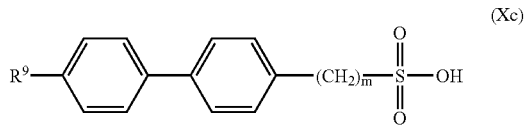
(Xc)

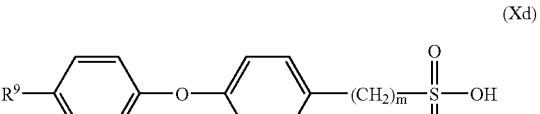
(Xd)

(Xe)

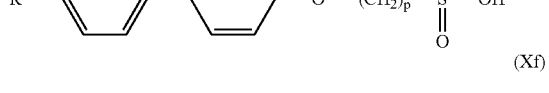
(Xf)

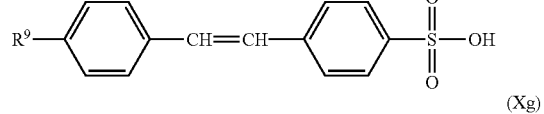
(Xg)

where $R^9$ is a radical as defined under 2.1. to 2.14.

To prepare the arylsulfonic acids of the formulae (Xa) and (Xb), the sulfonation process using concentrated sulfuric acid, optionally in the presence of a catalyst, sulfur trioxide and its addition compounds or halosulfonic acids, such as chlorosulfonic acid, described in Houben-Weyl *Methoden der Orzanischen Chemie* [Methods of Organic Chemistry], Volume 9, pp. 450–546, is preferably used. Particularly in the case of the diphenyl ethers of formula (Xb), the use of concentrated sulfuric acid and acetic anhydride as solvents (cf. C. M. Suter, *J. Am. Chem. Soc.* 53 (1931) 1114), or the reaction with excess chlorosulfonic acid (J. P. Bassin, R. Cremlyn and F. Swinbourne; *Phosphorus, Sulfur and Silicon* 72 (1992) 157) has proven suitable. Sulfonic acids according to the formulae (Xc), (Xd) or (Xe) can be prepared in a known manner by reacting the appropriate arylalkyl halide with sulfites such as sodium sulfite or ammonium sulfite in aqueous or aqueous/alcoholic solution, it being possible to accelerate the reaction in the presence of tetraorganoammonium salts such as tetrabutylammonium chloride.

Sulfonic acid derivatives according to formula (IV) used are in particular the sulfonyl chlorides. For their preparation, the corresponding sulfonic acids, also in the form of their salts such as sodium, ammonium or pyridinium salts, are reacted in a known manner with phosphorus pentachloride or thionyl chloride without or in the presence of a solvent such as phosphorus oxychloride or of an inert solvent such as methylene chloride, cyclohexane or chloroform, in general at reaction temperatures from 20° C. up to the boiling point of the reaction medium used.

The reaction of the sulfonic acid derivatives of formula (IV) with the amino acids of formulae (III), (V) or (VII) according to process variants a), b) or c) advantageously proceeds in the manner of the Schotten-Baumann reaction. Suitable bases for this purpose are particularly alkali metal hydroxides such as sodium hydroxide, but also alkali metal acetates, hydrogencarbonates, carbonates and amines. The reaction takes place in water or in a water-miscible or immiscible solvent such as tetrahydrofuran (THF), acetone, dioxane or acetonitrile, the reaction temperature in general being kept at from −10° C. to 50° C. In the case in which the reaction is carried out in anhydrous medium, tetrahydrofuran or methylene chloride, acetonitrile or dioxane in the presence of a base, such as triethylamine, N-methylmorpholine, N-ethyl or diisopropylethylamine is particularly used, possibly in the presence of N,N-dimethylaminopyridine as a catalyst.

In another variant, the aminocarboxylic acids of the formulae (III), (IV) or (VII) can first be converted into their silylated form with the aid of a silylating agent such as bis-trimethylsilyltrifluoroacetamide (BSTFA) and they can then be reacted with sulfonic acid derivatives to give compounds of formula (I).

The physiologically tolerable salts of the compounds of formula (I) capable of salt formation, including their stereoisomeric forms, are prepared in a manner known in the art. With basic reagents such as hydroxides, carbonates, hydrogencarbonates, alcoholates and also ammonia or organic bases (e.g., trimethyl- or triethylamine, ethanolamine or triethanolamine), or, alternatively, basic amino acids (e.g., lysine, ornithine or arginine), the carboxylic acids form stable alkali metal, alkaline earth metal or optionally substituted ammonium salts. If the compounds of formula (I) have basic groups, stable acid addition salts can also be prepared with strong acids. Those suitable for this purpose are both inorganic and organic acids such as hydrochloric, hydrobromic, sulfuric, phosphoric, methanesulfonic, benzenesulfonic, p-toluenesulfonic, 4-bromobenzenesulfonic, cyclohexylamidosulfonic, trifluormethylsulfonic, acetic, oxalic, tartaric, succinic or trifluoroacetic acid.

The invention also relates to pharmaceuticals comprising an efficacious amount of at least one compound of formula (I), a stereoisomeric form of the compound of formula (I), or of a physiologically tolerable salt of the compound or stereoisomeric form of the compound of formula (I), together with a pharmaceutically suitable and physiologically tolerable excipient, additive, or other active or inactive compounds and auxiliaries.

On account of the pharmacological properties, the compounds according to the invention are suitable for the prophylaxis and therapy of all those disorders in the course of which an increased activity of matrix-degrading metalloproteinases is involved. These include degenerative joint disorders such as osteoarthroses, spondyloses, chondrolysis after joint trauma or relatively long immobilization of the joint after meniscus or patella injuries or tears of the ligaments. Furthermore, these also include disorders of the connective tissue such as collagenoses, periodontal disorders, wound healing disorders and chronic disorders of the locomotory apparatus such as inflammatory, immunologically or metabolically related acute and chronic arthritides, arthropathies, myalgias and disorders of the bone metabolism. The compounds of formula (I) are furthermore suitable for the treatment of ulceration, atherosclerosis and stenoses. The compounds of formula (I) are furthermore suitable for the treatment of inflammations, carcinomatous disorders, formation of tumor metastases, cachexia, anorexia and septic shock. The pharmaceuticals according to the invention are in general administered orally or parenterally. Transmucosal (such as rectal administration) or transdermal administration is also possible.

The invention also relates to a process for the production of a pharmaceutical, which comprises bringing at least one compound of formula (I) into a suitable administration form using a pharmaceutically suitable and physiologically tolerable excipient and, if appropriate, other suitable active or inactive compounds, additives or auxiliaries.

Suitable solid or pharmaceutical preparation forms are, for example, granules, powders, coated tablets, tablets, (micro)capsules, suppositories, syrups, juices, suspensions, emulsions, drops or injectable solutions and also preparations with protracted release of active compound, in whose preparation customary auxiliaries, such as excipients, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactoprotein, gelatin, starch, cellulose and its derivatives, animal and vegetable oils such as fish liver oil, sunflower, groundnut or sesame oil, polyethylene glycol and solvents such as, for example, sterile water and mono- or polyhydric alcohols such as glycerol.

The pharmaceutical preparations are preferably prepared and administered in dose units, each unit as active constituent containing a specific dose of the compound of formula (I) according to the invention. In solid dose units such as tablets, capsules, coated tablets or suppositories, this dose can be up to approximately 1000 mg, with the currently preferred dose being approximately 50 to 300 mg, and in injection solutions in ampoule form up to approximately 300 mg, with the currently preferred dose being approximately 10 to 100 mg.

For the treatment of an adult patient weighing approximately 70 kg—depending on the efficacy of the compounds according to formula (I), daily doses of approximately 20 mg to 1000 mg, preferably approximately 100 mg to 500 mg, of active compound are indicated. Under certain circumstances, however, higher or lower daily doses may be appropriate. The daily dose can be administered both by single administration in the form of an individual dose unit or else of several smaller dose units and by multiple administration of subdivided doses at specific intervals.

$^1$H-NMR spectra have been recorded on a 200 MHz apparatus from Varian, as a rule using tetramethylsilane (TMS) as an internal standard and at room temperature (RT). The solvents used are in each case indicated. As a rule, final products are determined by mass-spectroscopic methods (FAB-, ESI-MS). Temperature data in degrees Celsius, RT means room temperature (22–26° C.). Abbreviations used are either explained or correspond to the customary conventions.

EXAMPLE 1

N-(Phenoxybenzenesulfonyl) homoserine

Prepared according to process variant a): 10 g (54.9 mmol) of D,L-homoserine lactone are treated with ice-cooling with 50 ml of 1N NaOH and 50 ml of tetrahydrofuran (THF). 16.0 g (59.5 mmol) of phenoxybenzenesulfonyl chloride in 50 ml of THF are added dropwise at 5° C. with stirring, after half of the addition the reaction mixture being treated with 7.1 g (54.9 mmol) of diisopropylethylamine. After stirring overnight, the mixture is adjusted to pH=5.5 using 2N HCl and extracted several times with ethyl acetate. The combined organic phases are dried over sodium sulfate, filtered, and evaporated under reduced pressure. Recrystallization from glacial acetic acid/petroleum ether affords the abovementioned compound.

Yield: 18.3 g (73% of theory) Melting point: 134° C. $^1$H-NMR (DMSO-d$_6$): 1.6–1.85 (m, 2H); 3.2–3.45 (m, 3H); 3.75–3.95 (m, 1H); 7.0–8.1 (m, 9H)

EXAMPLE 2

(2R)-1-(4-Chlorobiphenylsulfonyl)-4-cis-hydroxyproline

Prepared according to process variant a): 2 g (15.2 mmol) of D-cis-hydroxyproline are dissolved in dry acetonitrile and heated under reflux for 2 hours together with 12.1 ml (46.7 mmol, 3.1 equivalents) of BSTFA (bis-trimethylsilyltrifluoroacetamide). The mixture is then treated with 4.4 g (15.2 mmol) of 4-chlorobiphenylsulfonyl chloride in 15 ml of acetonitrile and is left under reflux for a further 4 hours. A thick, white precipitate of the O-silylated-N-sulfonated compound is formed. After cooling of the suspension and completion of the precipitation, this is separated off and well dried under reduced pressure. The yield of the reaction is quantitative.

For desilylation, 100 mg of the O-silylated compound are taken up in 10 ml of methanol (MeOH) and stirred at room temperature (RT) for 2 hours with 10 ml of 1N HCl with addition of 100 mg of KF. Filtration of the precipitate with suction and drying under reduced pressure affords the abovementioned product.

Yield: 61 mg (84% of theory) $^1$H-NMR (DMSO-d$_6$): 1.8–2.2 (m, 2H); 3.15 (m, 1H); 3.3 (dd, 2H); 4.0 (m, 1H); 4.3 (dd, 1H); 7.6; 7.8 (2d, 4H); 7.9 (s, 4H)

EXAMPLE 29

(R)-N-(4-Chlorobiphenylsulfonyl)tryptophan

Prepared according to process variant b):

(a) The (R)-N-(4-Chlorobiphenylsulfonyl)tryptophan methyl ester 5.1 g (20 mmol) of D-tryptophan methyl ester hydrochloride are suspended in 50 ml of dry acetonitrile, treated with 2.0 g (20 mmol) of triethylamine and stirred at RT. After addition of 6.2 ml (24 mmol) of BSTFA, the mixture is stirred at 80° C. for 2 hours, then 5.75 g (20 mmol) of 4-chlorobiphenylsulfonyl chloride in 50 ml of acetonitrile and a further 2.0 g of TEA are added dropwise and the mixture is kept at 80° C. for 2 hours. After cooling to RT, 100 ml of 1N HCl are added to the reaction mixture with stirring, a crystalline precipitate being deposited. Recrystallization from methanol/water affords the abovementioned methyl ester.

Yield: 6.8 g (92% of theory) Melting point: 189° C.

(b) (R)-N-(4-Chlorobiphenylsulfonyl)tryptophan 2.34 g (5 mmol) of the above methyl ester are dissolved in 30 ml of methanol and, after addition of 10 ml of 1N NaOH, stirred at 40° C. for 6 hours. Adjustment of the solution to pH=6 using 1N HCl affords the abovementioned carboxylic acid in crystalline form.

Yield: 1.8 g (81% of theory) Melting point: 138° C. to 140° C. $^1$H-NMR (DMSO-d$_6$): 2.8–2.92 (m, 1H), 3.0–3.12 (m, 1H), 3.83–3.97 (m, 1H), 6.85–7.8 (m, 13 H), 8.3 (d, 1H), 10.75 (s, 1H), 12.4 (s, 1H)

The examples mentioned in Table 1 which follows have been prepared analogously to above Examples 1, 2 and 29.

TABLE 1

| Example | Structure | Note | M.p. (° C.) | MS (M + H) |
| --- | --- | --- | --- | --- |
| 1 | 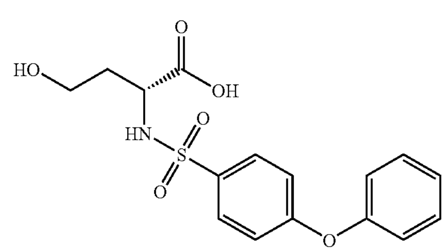 | racemate | 134 | |

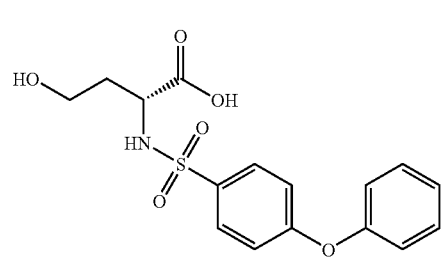

TABLE 1-continued

| Example | Structure | Note | M.p. (° C.) | MS (M + H) |
|---------|-----------|------|-------------|------------|
| 2 | 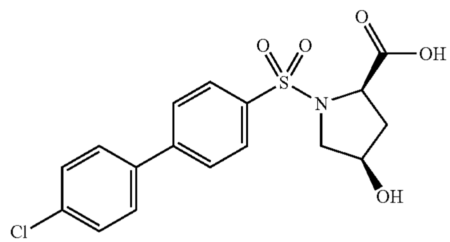 | | | 382.1 (M − 1) |
| 3 | 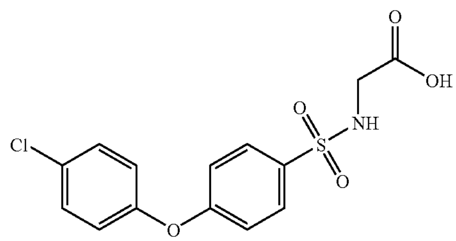 | | 162–164 | |
| 4 | 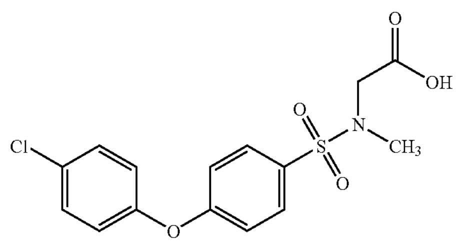 | | 128–130 | |
| 5 | 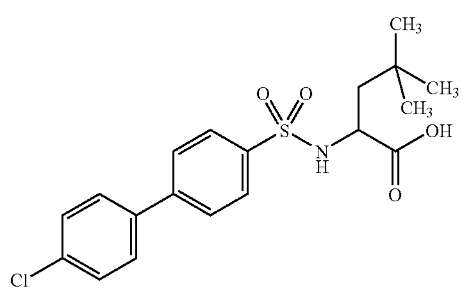 | racemate | | 396.1 |
| 6 | 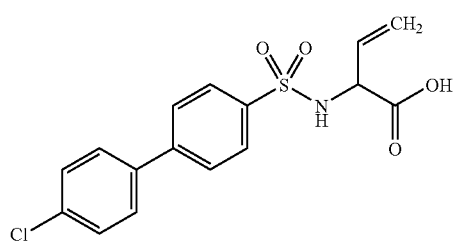 | racemate | | 352.1 (M − 1) |
| 7 | 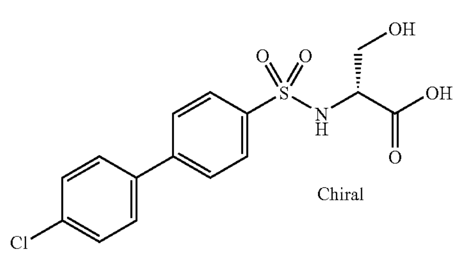 | Chiral | | 356.1 |

TABLE 1-continued
| Example | Structure | Note | M.p. (° C.) | MS (M + H) |
|---|---|---|---|---|
| 8 | 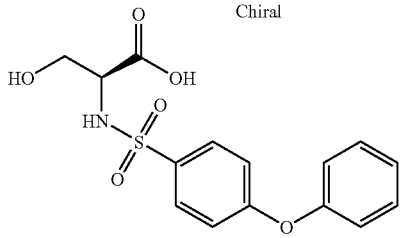 | Chiral | 202–203 | |
| 9 | 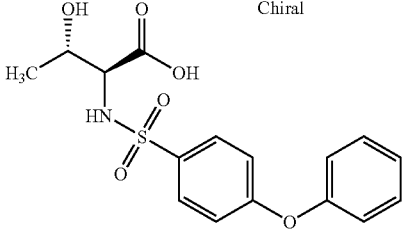 | Chiral | 96–98 | |
| 10 | 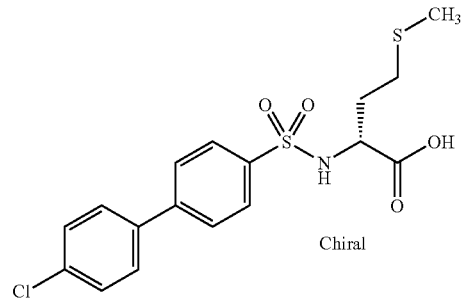 | Chiral | | 400.1 (M − 1) |
| 11 | 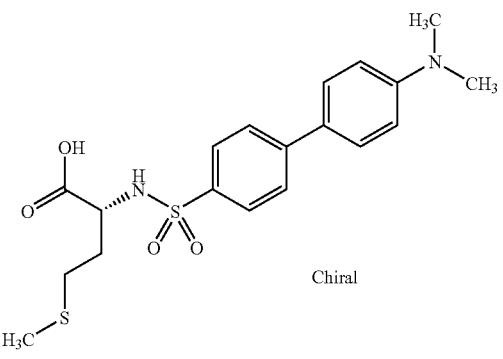 | Chiral | 180–186 (amorphous) | 409.2 |
| 12 | 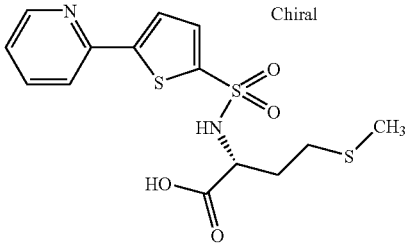 | Chiral | 115–125 (amorphous) | 373.1 |

TABLE 1-continued
| Example | Structure | Note | M.p. (° C.) | MS (M + H) |
|---|---|---|---|---|
| 13 | 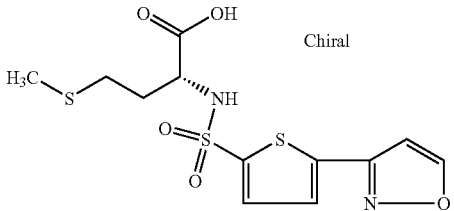 Chiral | | 70–76 (amorphous) | 363.0 |
| 14 | 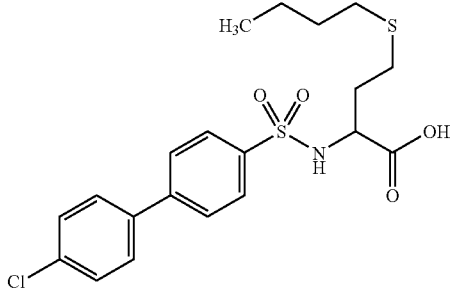 | racemate | | 442.1 |
| 15 | 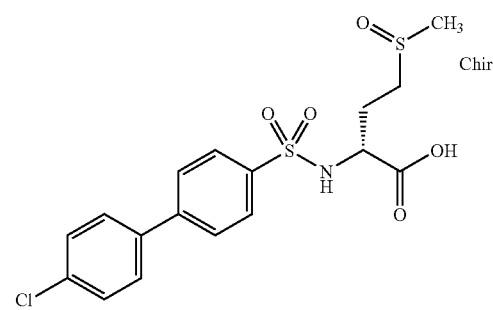 Chiral | | | 416.1 (M − 1) |
| 16 | 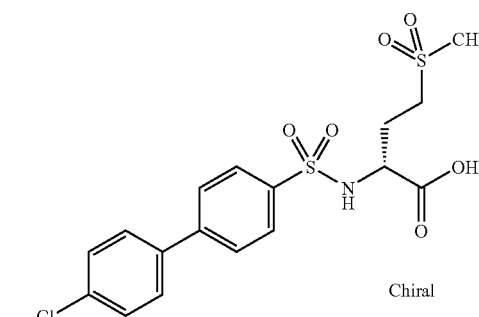 Chiral | | | 432.0 (M − 1) |
| 17 | 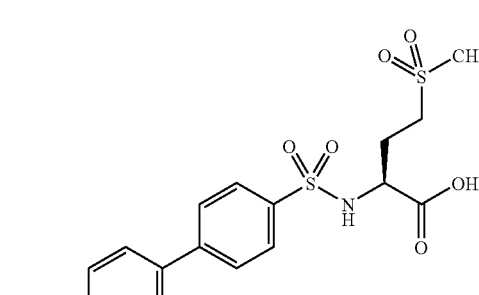 Chiral | | | 432.0 (M − 1) |

TABLE 1-continued

| Example | Structure | Note | M.p. (° C.) | MS (M + H) |
|---------|-----------|------|-------------|------------|
| 18 | 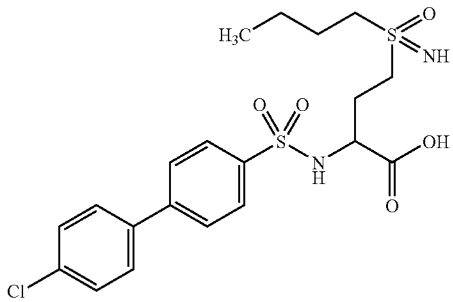 | racemate | | 473.1 |
| 19 | 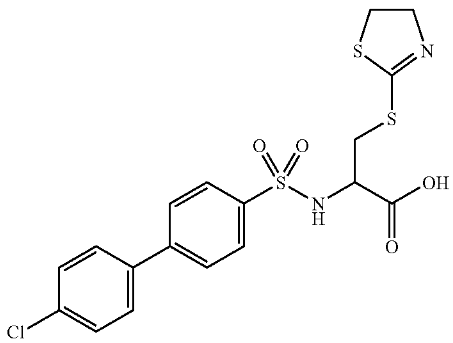 | racemate | | 457.0 |
| 20 | 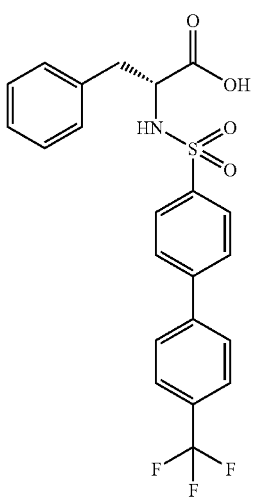 | Chiral | 159–162 | 449.1 |
| 21 | 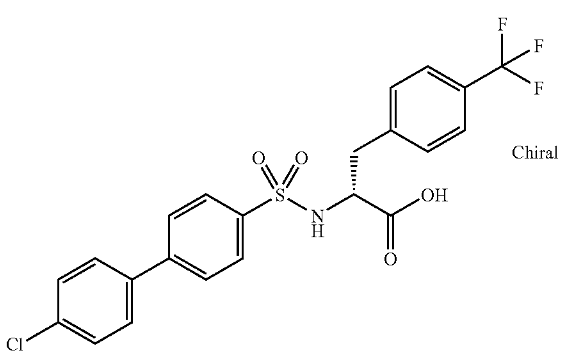 | Chiral | | 482.0 (M − 1) |

TABLE 1-continued

| Example | Structure | Note | M.p. (° C.) | MS (M + H) |
|---|---|---|---|---|
| 22 | 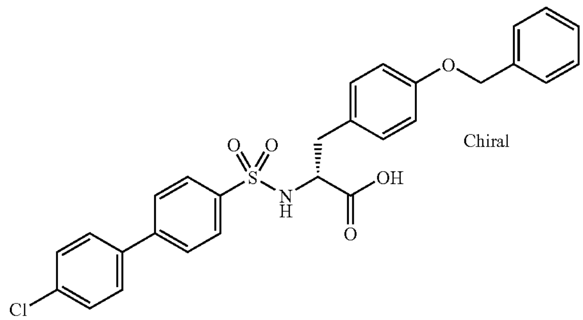 | Chiral | | 520.1 (M − 1) |
| 23 | 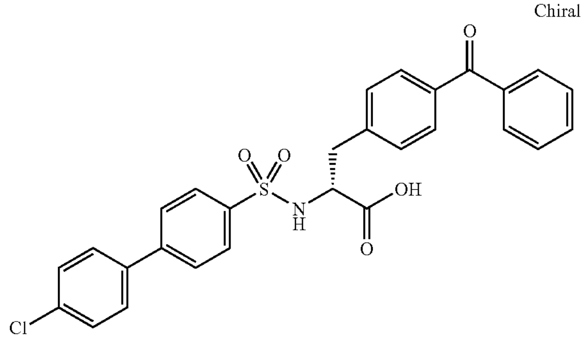 | Chiral | | 520.1 |
| 24 | 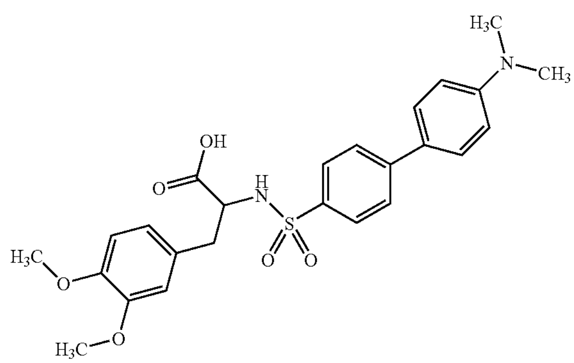 | racemate | 230.0 (amorphous) | 485.3 |
| 25 | 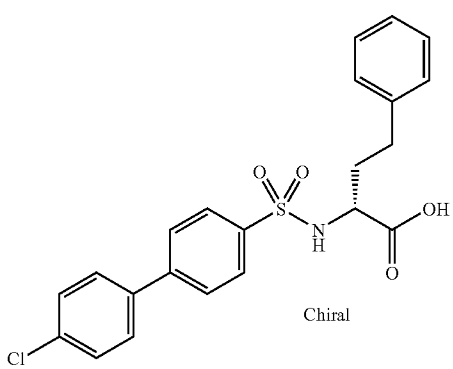 | Chiral | | 430.1 |

TABLE 1-continued

| Example | Structure | Note | M.p. (° C.) | MS (M + H) |
|---|---|---|---|---|
| 26 | 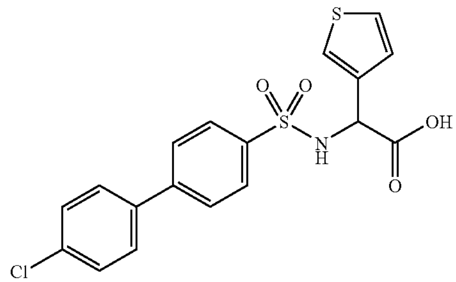 | racemate | | 408.0 |
| 27 | 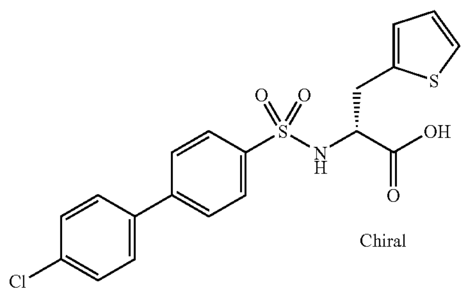 | Chiral | >200 (dec.) | |
| 28 | 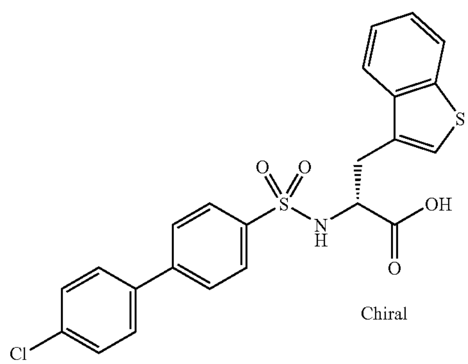 | Chiral | | 472.1 |
| 29 | 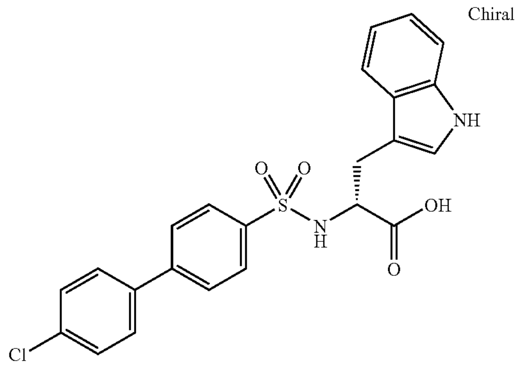 | Chiral | | 455.1 (M − 1) |
| 30 | 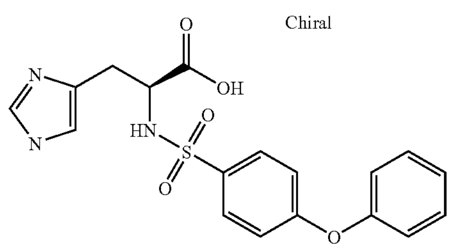 | Chiral | 183–185 | |

TABLE 1-continued

| Example | Structure | Note | M.p. (° C.) | MS (M + H) |
|---------|-----------|------|-------------|------------|
| 31 | 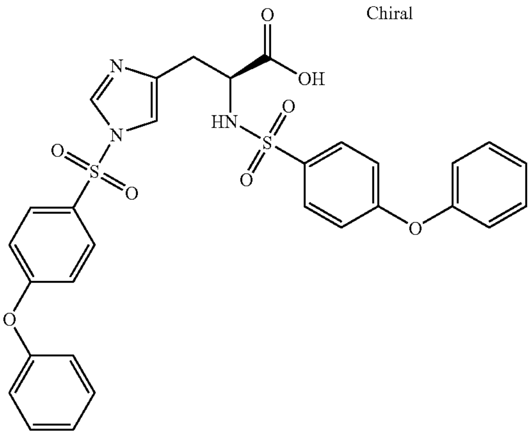 | Chiral | 120–122 | |
| 32 | 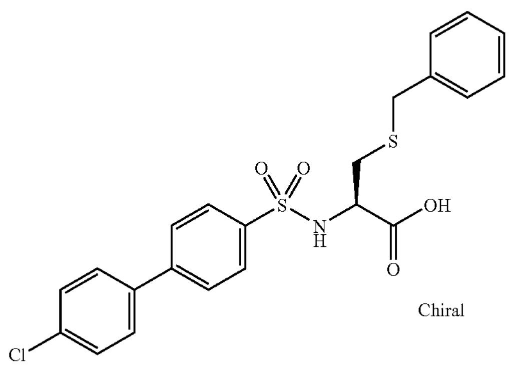 | Chiral | | 462.1 (M − 1) |
| 33 | 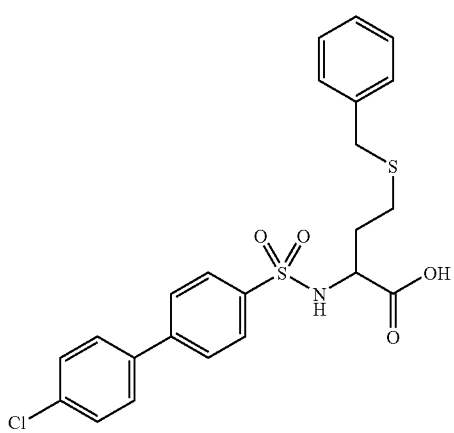 | racemate | | 476.1 |
| 34 | 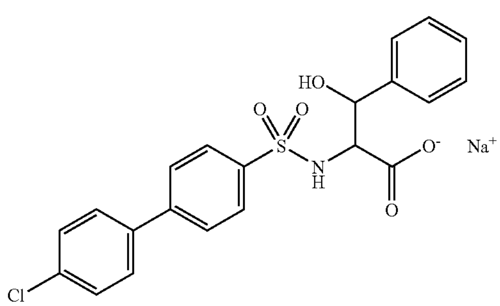 | DL-threo-diastereomer mixture | | 454.1 (M − 1) |

TABLE 1-continued

| Example | Structure | Note | M.p. (° C.) | MS (M + H) |
|---|---|---|---|---|
| 35 | 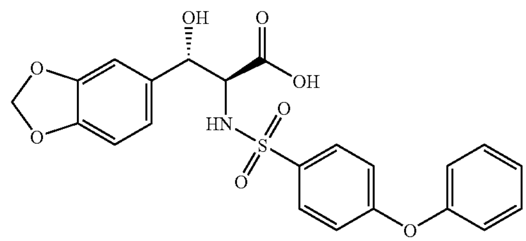 | racemate | 176 | |
| 36 | 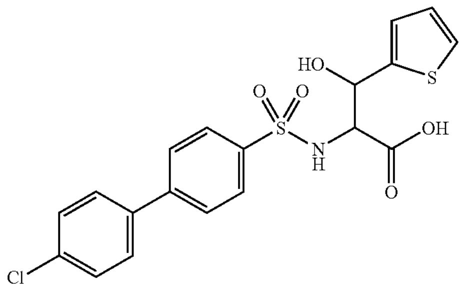 | diastereomer mixture | | 436.0 (M − 1) |
| 37 | 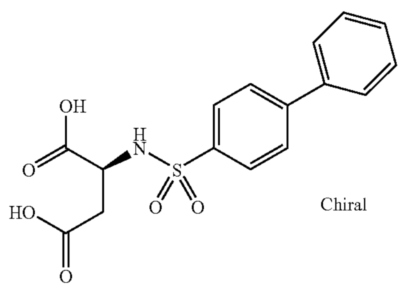 | S isomer | 186.7 | 348.1 (M − 1) |
| 38 | 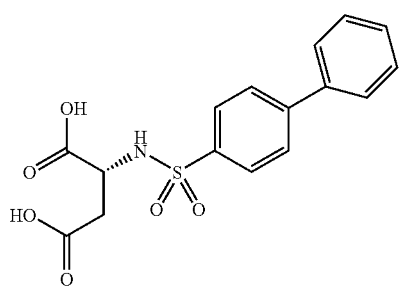 | R isomer | >55 (amorphous) | 350.1 |
| 39 | 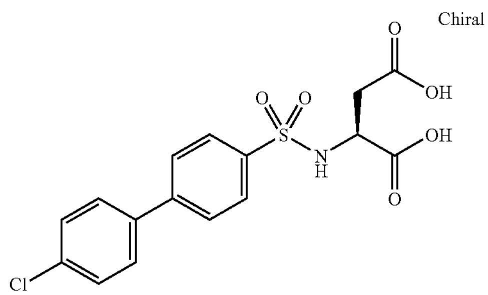 | Chiral | | 384.0 (M − 1) |

TABLE 1-continued
| Example | Structure | Note | M.p. (° C.) | MS (M + H) |
|---|---|---|---|---|
| 40 | 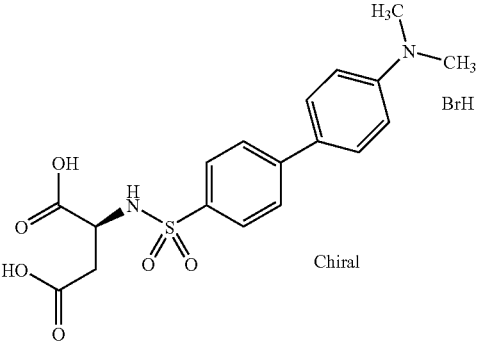 Chiral | BrH | 121–127 (amorphous) | 393.2 |
| 41 | 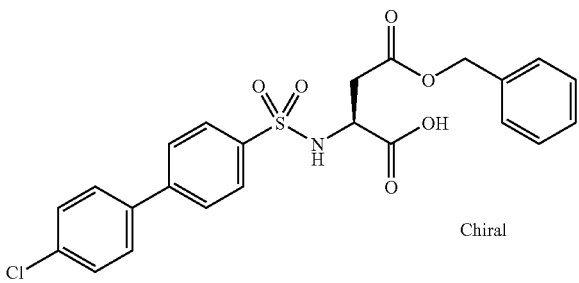 Chiral | | | 472.1 |
| 42 | 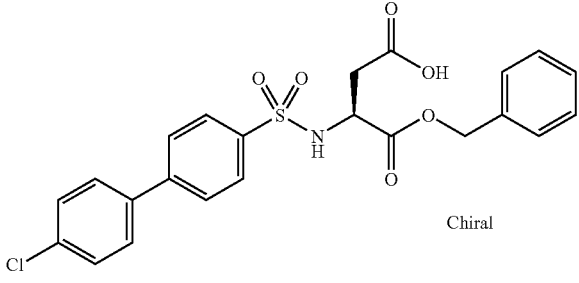 Chiral | | | 474.1 |
| 43 | 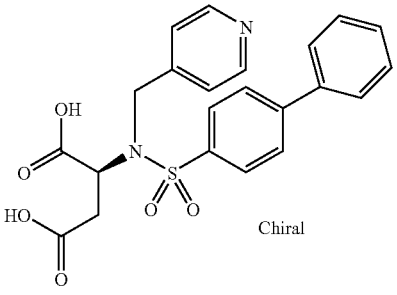 Chiral | | 105 | 439.1 (M − 1) |
| 44 | 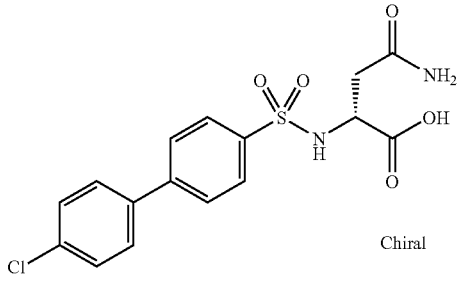 Chiral | | | 383.1 |

TABLE 1-continued

| Example | Structure | Note | M.p. (° C.) | MS (M + H) |
|---------|-----------|------|-------------|------------|
| 45 | 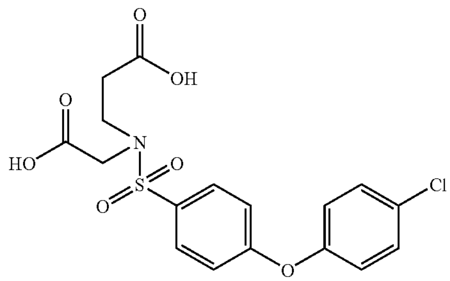 | | 169–171 | |
| 46 | 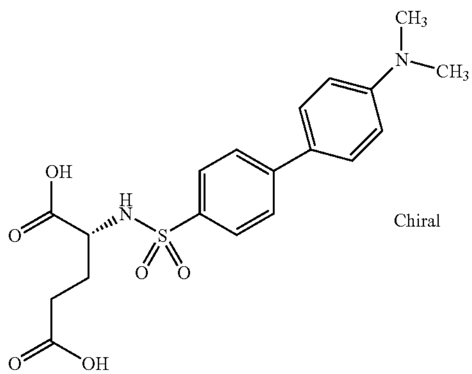 | Chiral | 165.0 (amorphous) | 407.2 (M − 1) |
| 47 | 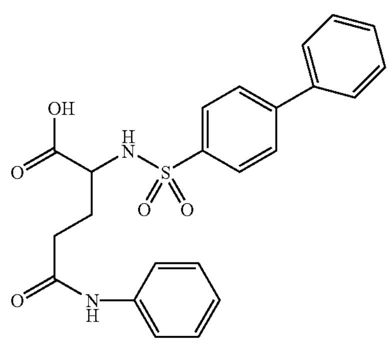 | racemate | 227–230 | 439.2 |
| 48 | 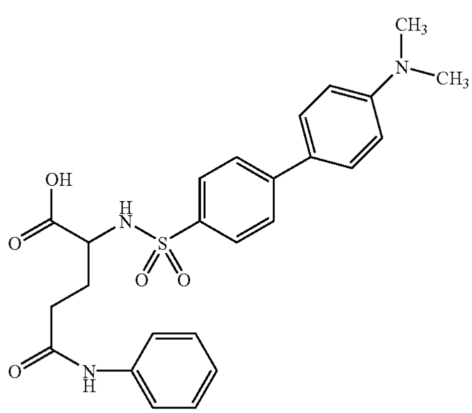 | racemate | 212–214 | |

TABLE 1-continued
| Example | Structure | Note | M.p. (° C.) | MS (M + H) |
| --- | --- | --- | --- | --- |
| 49 | 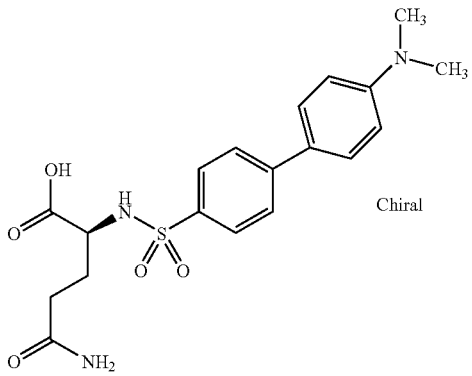 Chiral | | 213–215 | 406.2 |
| 50 | 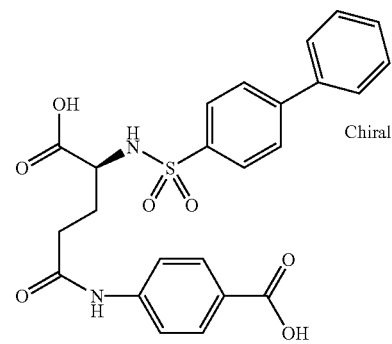 Chiral | | 266.0 | 483.2 |
| 51 | 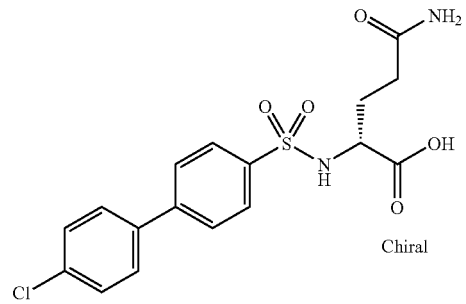 Chiral | | | 395.1 (M − 1) |
| 52 | 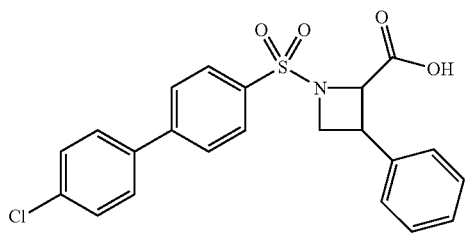 | trans-diastereomer pair | | 428.1 (M − 1) |
| 53 | 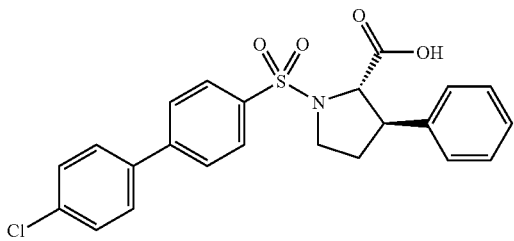 | (2S, 3R)-isomer | | 442.2 (M − 1) |

TABLE 1-continued

| Example | Structure | Note | M.p. (° C.) | MS (M + H) |
|---|---|---|---|---|
| 54 | 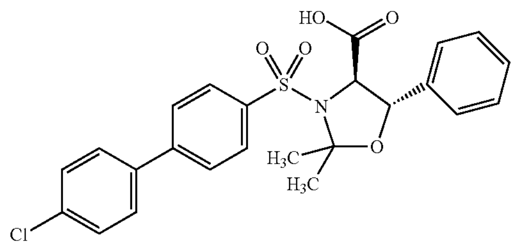 | D,L-threo-diastereomer pair | | 472.1 (M − 1) |
| 55 | 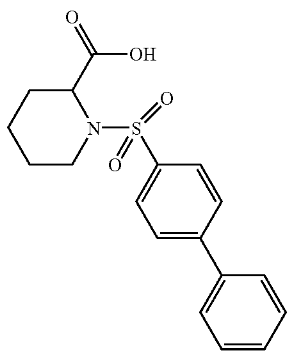 | racemate | 174.5–175.5 | 346.1 |
| 56 | 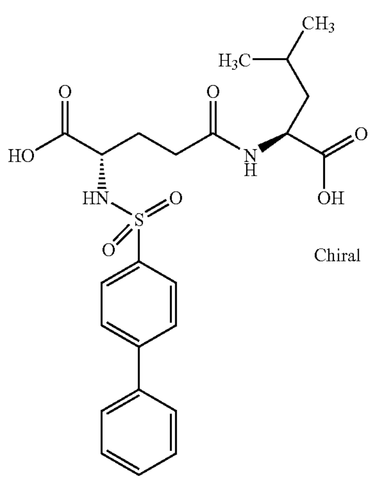 | in each case S isomer | 93–95 | 477.2 |
| 57 | 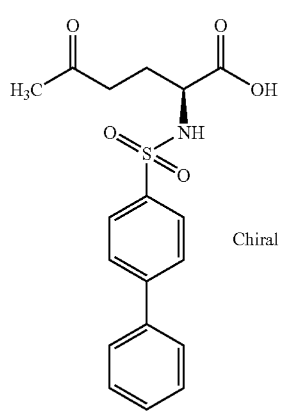 | S isomer | 183.4 | 363.2 |

TABLE 1-continued
| Example | Structure | Note | M.p. (° C.) | MS (M + H) |
| --- | --- | --- | --- | --- |
| 58 | 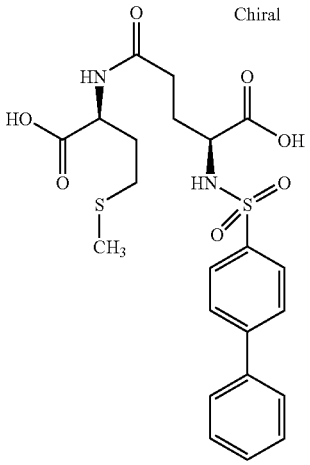 | S isomer | 159–161 | 495.2 |
| 59 | 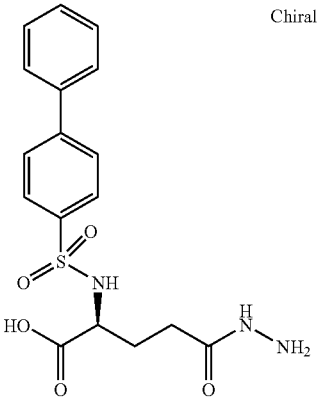 | S isomer | 205–207 | 378.2 |
| 60 | 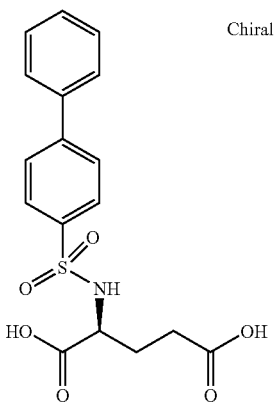 | S isomer | 145–146 | 362.1 (M − H) |

TABLE 1-continued
| Example | Structure | Note | M.p. (° C.) | MS (M + H) |
|---|---|---|---|---|
| 61 | 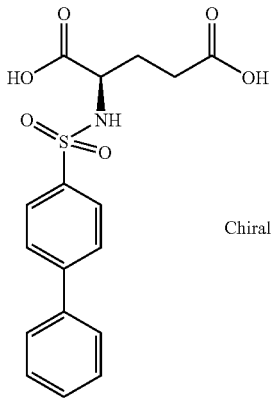 Chiral | R isomer | 155–158 | 362.1 (M − H) |
| 62 | 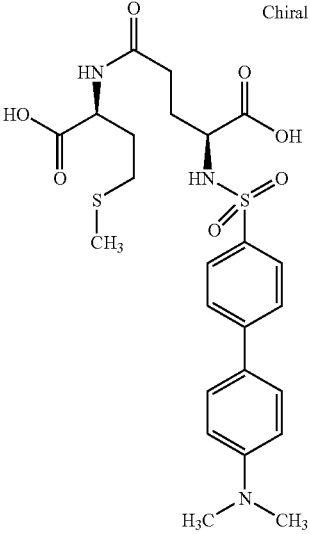 Chiral | in each case S isomer | 121 | 538.2 |
| 63 | 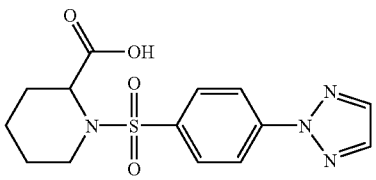 | racemate | 195–196 | 337.2 |
| 64 | 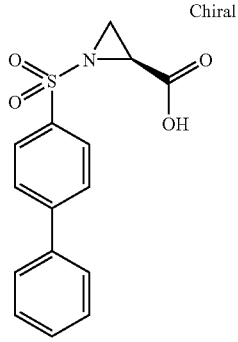 Chiral | S isomer | 138–139 | 304.1 |

TABLE 1-continued

| Example | Structure | Note | M.p. (° C.) | MS (M + H) |
|---------|-----------|------|-------------|------------|
| 65 | 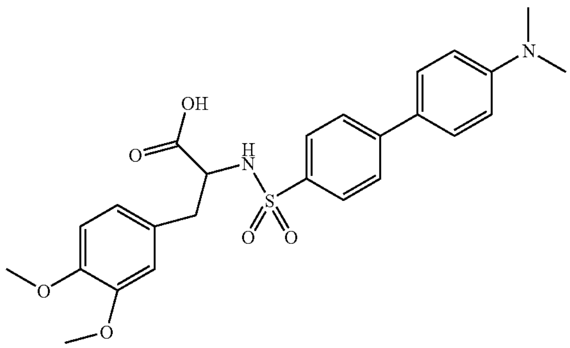 | racemate | >230 (dec.) | 485.3 |
| 66 | 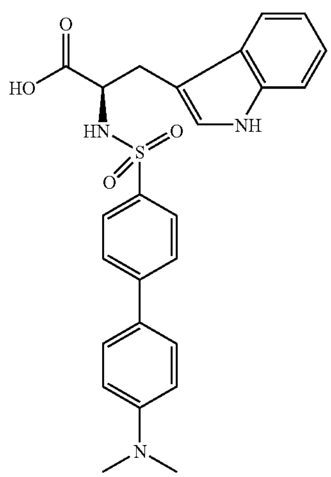 | R isomer | 258–260 | 464.2 |
| 67 | 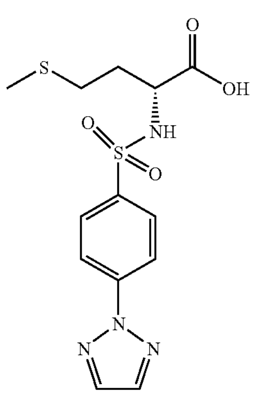 | R isomer | 155.5–156.5 | 357.1 |

TABLE 1-continued
| Example | Structure | Note | M.p. (° C.) | MS (M + H) |
|---|---|---|---|---|
| 68 | 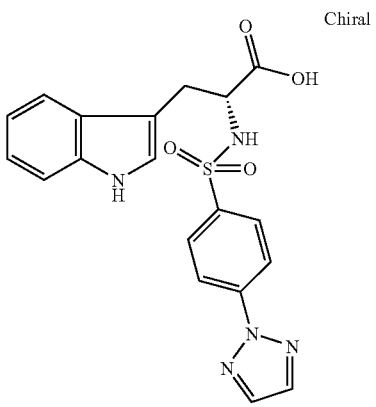 | R isomer | 131–134 | 412.1 |
| 69 | 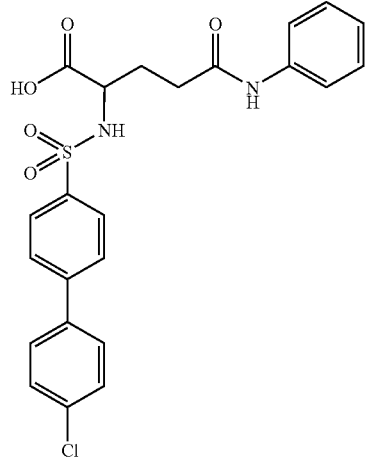 | racemate | 238–239 | 473.1/475.1 |
| 70 | 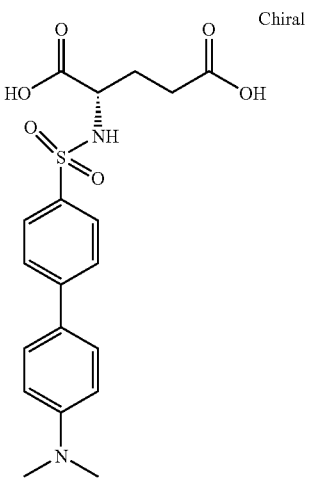 | S isomer | >108 (dec.) | 407.2 |

TABLE 1-continued
| Example | Structure | Note | M.p. (° C.) | MS (M + H) |
|---|---|---|---|---|
| 71 | 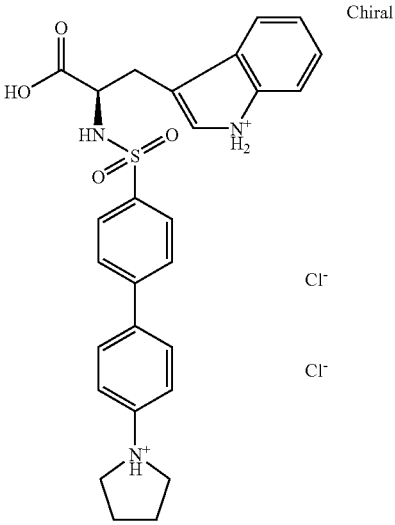 | R isomer | >145 (dec.) | 490.3 |
| 72 | 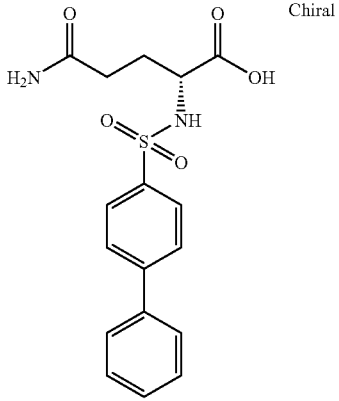 | R isomer | 179.180.5 | 363.1 |
| 73 | 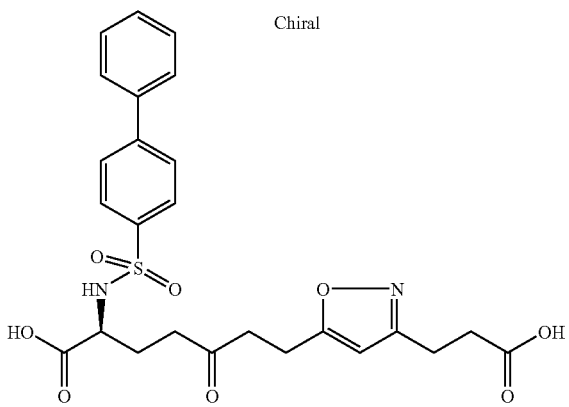 | S isomer | 181.5–182.5 | 516.3 |

TABLE 1-continued
| Example | Structure | Note | M.p. (° C.) | MS (M + H) |
|---------|-----------|------|-------------|------------|
| 74 | 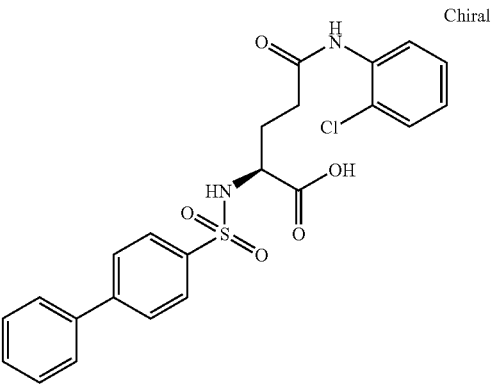 | S isomer | 187.5–188.5 | 473.2 |
| 75 | 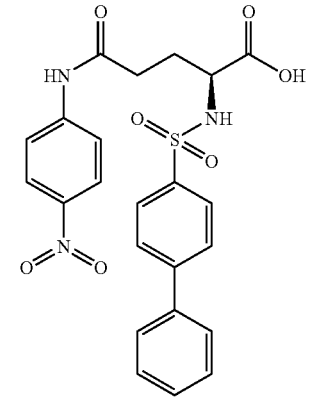 | S isomer | 232–233 | 484.2 |
| 76 | 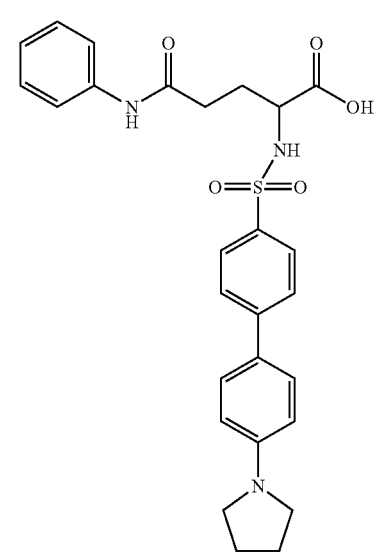 | racemate | 234–236 (dec.) | 508.2 |

TABLE 1-continued
| Example | Structure | Note | M.p. (° C.) | MS (M + H) |
| --- | --- | --- | --- | --- |
| 77 | 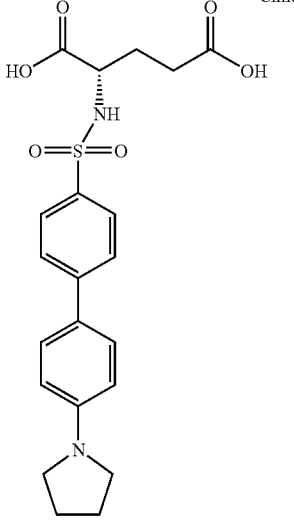 Chiral | S isomer | >220 (dec.) | 433.3 |
| 78 | 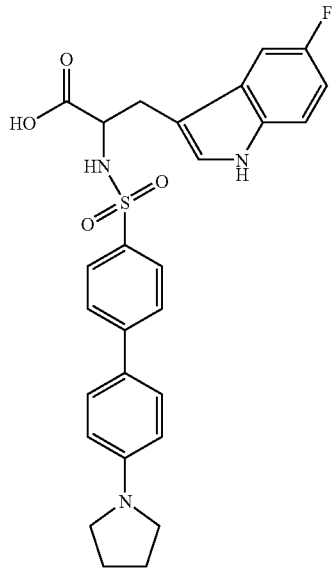 | racemate | >230 (dec.) | 508.2 |
| 79 | 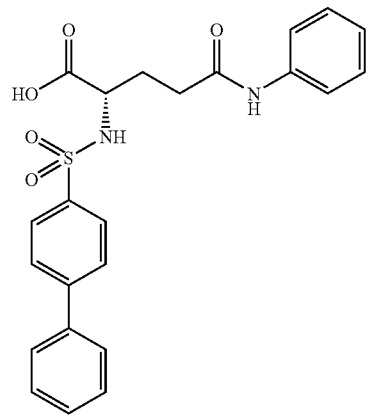 Chiral | S isomer | 234.5–235.5 | 439.2 |

TABLE 1-continued
| Example | Structure | Note | M.p. (° C.) | MS (M + H) |
|---|---|---|---|---|
| 80 | 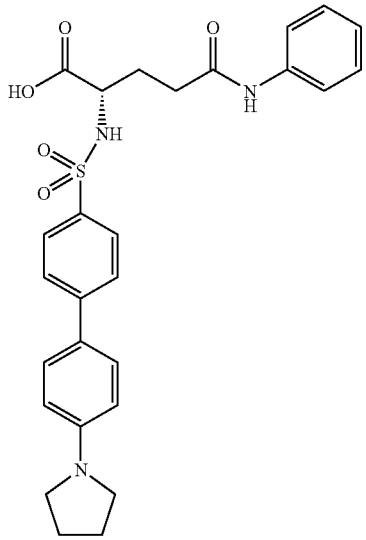 Chiral | S isomer | >228 (dec.) | 508.3 |
| 81 | 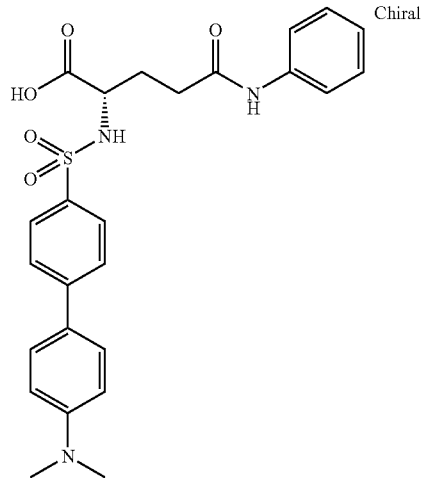 Chiral | S isomer | 240.5–241.5 (dec.) | 482.3 |
| 82 | 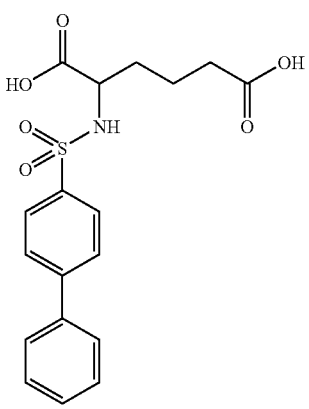 | racemate | 171.5–172 | 378.2 |

TABLE 1-continued
| Example | Structure | Note | M.p. (° C.) | MS (M + H) |
| --- | --- | --- | --- | --- |
| 83 | 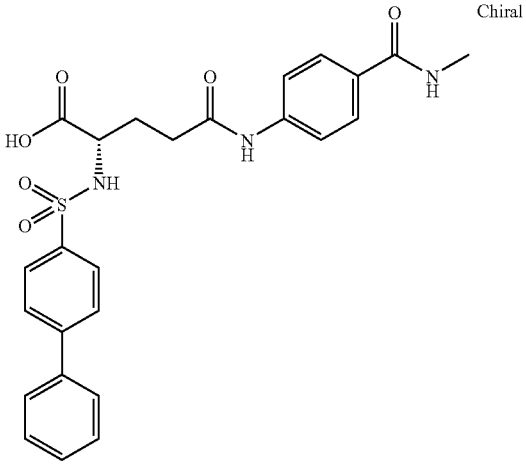 | S isomer | 250–250.5 | 496.2 |
| 84 | 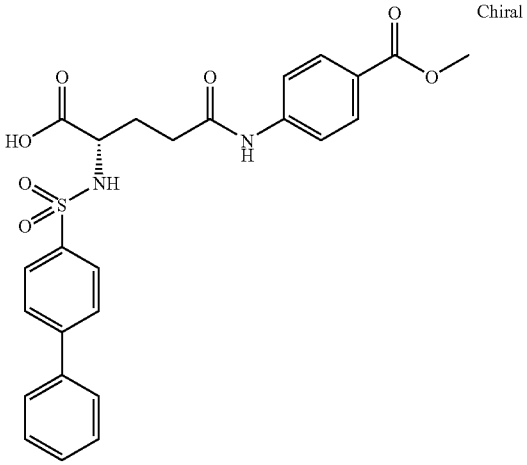 | S isomer | 245–245.5 | 497.2 |
| 85 | 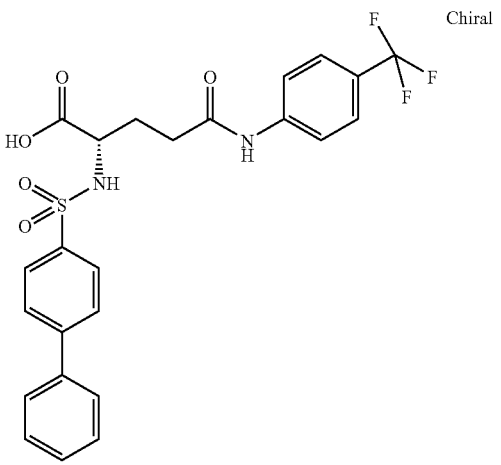 | S isomer | 265 | 507.3 |

TABLE 1-continued
| Example | Structure | Note | M.p. (° C.) | MS (M + H) |
|---|---|---|---|---|
| 86 | 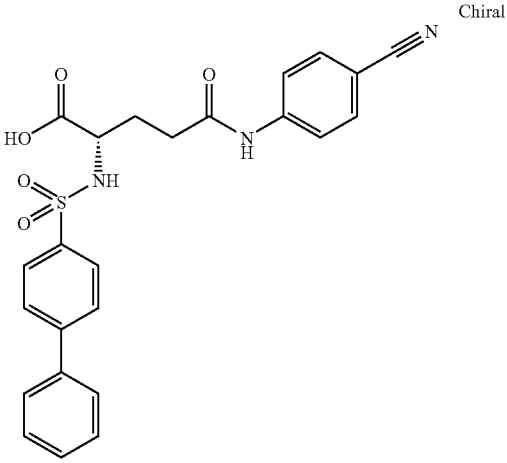 | S isomer | 220 | 464.0 |
| 87 | 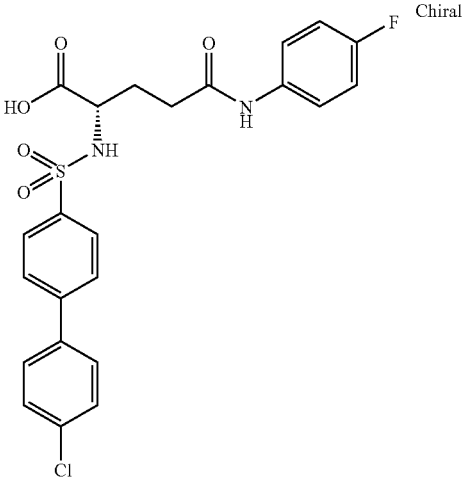 | S isomer | >245 (dec.) | 491.0 |
| 88 | 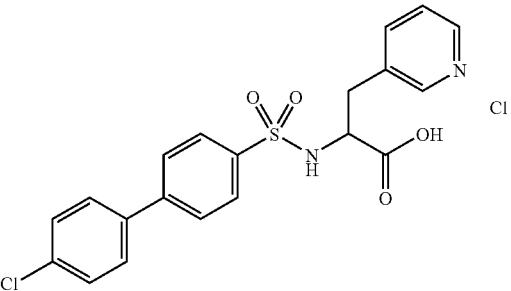 | racemate | | 417.1 |

TABLE 1-continued

| Example | Structure | Note | | M.p. (° C.) | MS (M + H) |
|---|---|---|---|---|---|
| 89 | Chiral | S isomer | | 219–221 | 469.2 |
| 90 | Chiral | S isomer | | >245 (dec.) | 526.3 |
| 91 | Chiral | S isomer | | >258 (dec.) | 457.0 |

TABLE 1-continued
| Example | Structure | Note | M.p. (° C.) | MS (M + H) |
| --- | --- | --- | --- | --- |
| 92 | 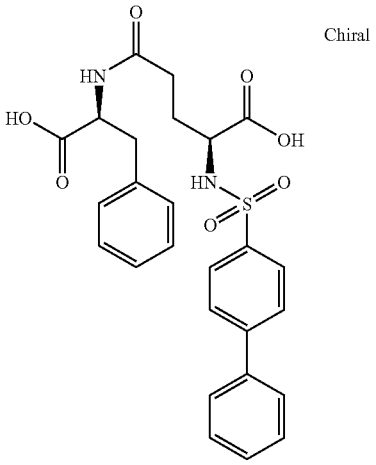 | in each case S isomer | 123.5–124.5 | 511.2 |
| 93 | 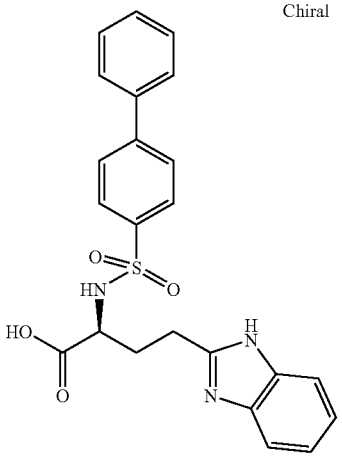 | S isomer | >250.0 (dec.) | 436.3 |
| 94 | 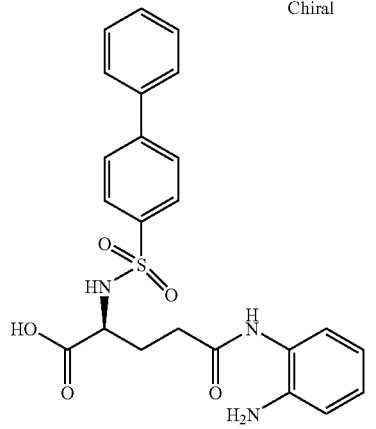 | S isomer | 111–112 | 545.2 |

TABLE 1-continued
| Example | Structure | Note | M.p. (° C.) | MS (M + H) |
|---|---|---|---|---|
| 95 | 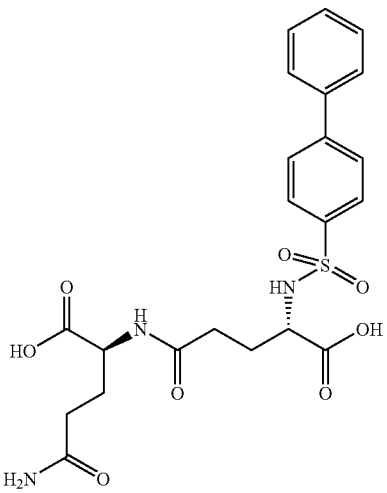 | in each case S isomer | >110 (dec.) | 492.2 |
| 96 | 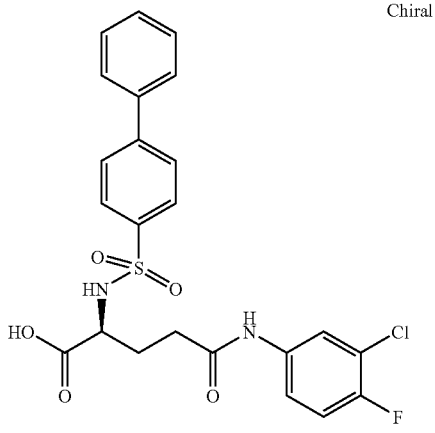 | S isomer | >245 (dec.) | 491.0 |
| 97 | 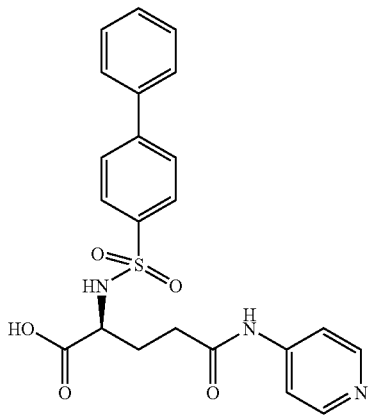 | S isomer | >290 (dec.) | 440.1 |

TABLE 1-continued

| Example | Structure | Note | M.p. (° C.) | MS (M + H) |
| --- | --- | --- | --- | --- |
| 98 | 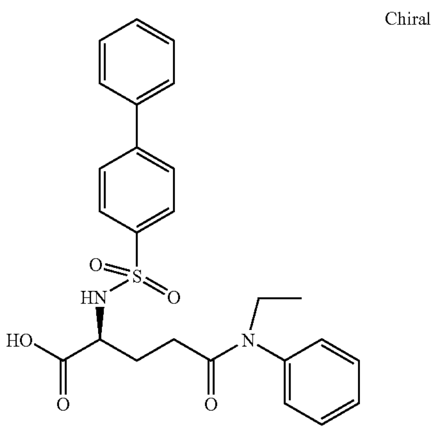 | S isomer | >155 (dec.) | 465.0 (M − 1) |
| 99 | 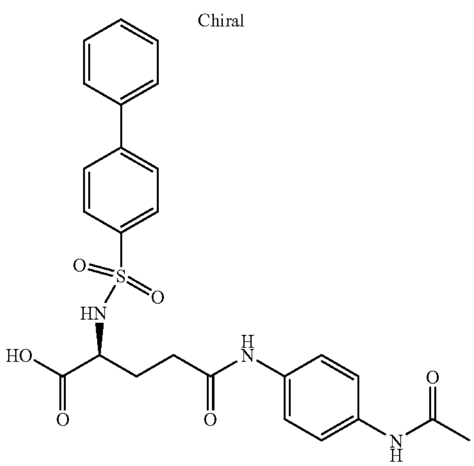 | S isomer | >230 (dec.) | 496.2 |
| 100 | 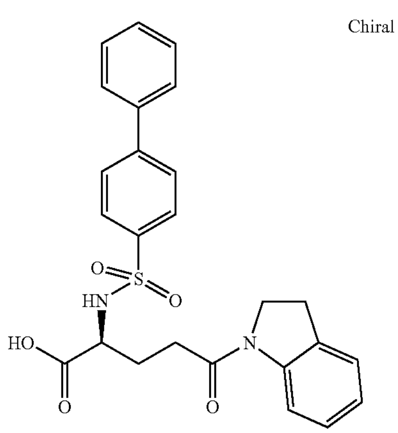 | S isomer | 182.5–183.5 | 462.9 (M − 1) |

TABLE 1-continued

| Example | Structure | Note | M.p. (° C.) | MS (M + H) |
| --- | --- | --- | --- | --- |
| 101 | 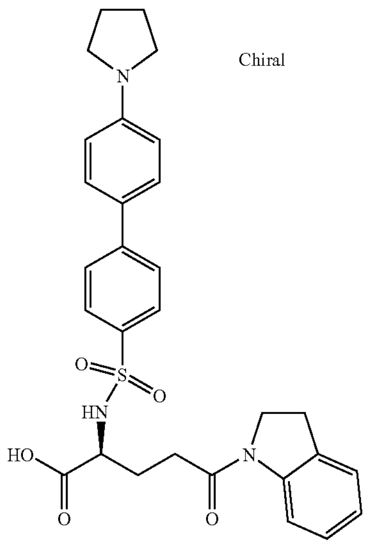 | S isomer | >130 (dec.) | 532.2 (M − 1) |
| 102 | 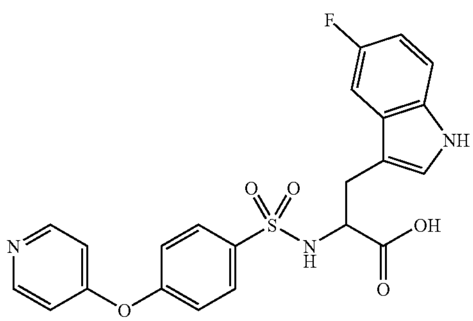 | S isomer | | 456.1 |
| 103 | 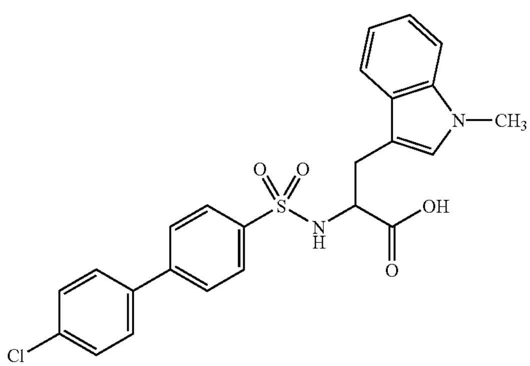 | racemate | | 469.1 |
| 104 | 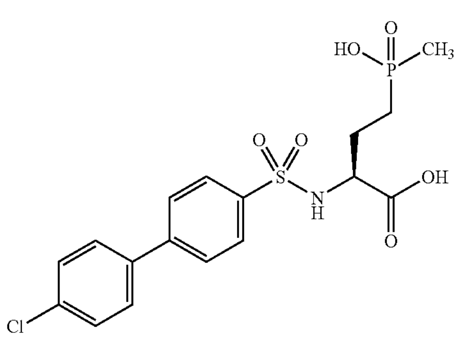 | S isomer | | 432.1 |

TABLE 1-continued

| Example | Structure | Note | M.p. (° C.) | MS (M + H) |
|---------|-----------|------|-------------|------------|
| 105 | 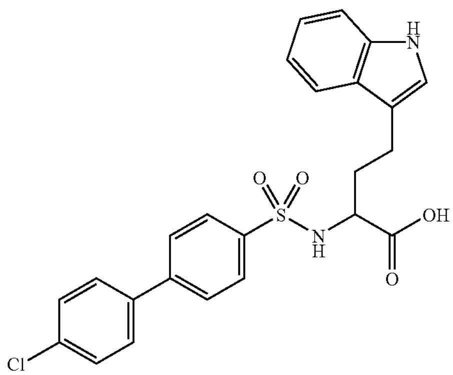 | racemate | | 469.2 |
| 106 | 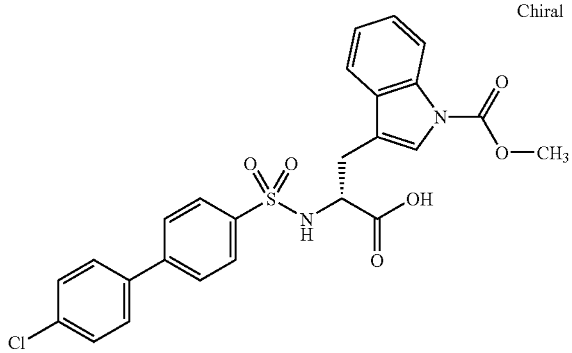 | Chiral R isomer | | 513.2 |
| 107 | 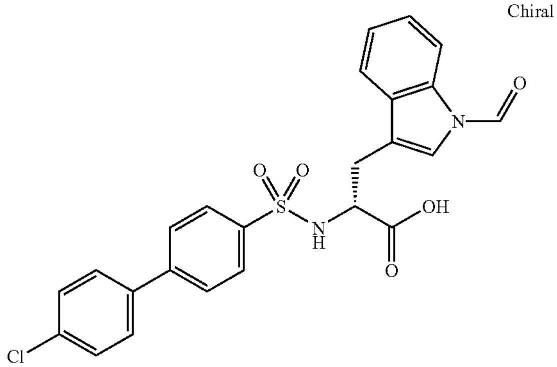 | Chiral R isomer | | 583.2 |
| 108 | 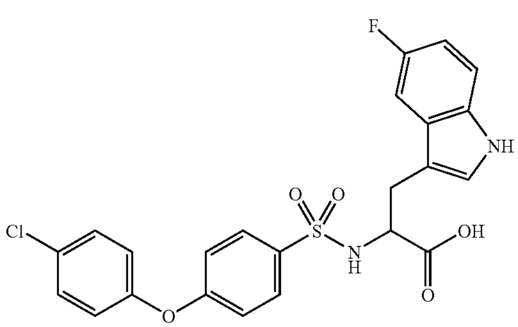 | racemate | | 489.1 |

Pharmacological Examples

Preparation and determination of the enzymatic activity of the catalytic domains of human stromelysin and of neutrophil collagenase:

The enzymes stromelysin (MMP-3) and neutrophil collagenase (MMP-8) were prepared according to Ye et al. (*Biochemistry;* 31 (1992) pages 11231–11235). To measure the enzyme activity or the enzyme inhibitor action, 70 μl of buffer solution and 10 μl of enzyme solution are incubated for 15 min with 10 μl of a 10% strength (v/v) aqueous dimethyl sulfoxide solution, which optionally contains the enzyme inhibitor. After addition of 10 μl of a 10% strength (v/v) aqueous dimethyl sulfoxide solution which contains 1 mmol/L of the substrate, the enzyme reaction is monitored by fluorescence spectroscopy (328 nm (ex)/393 nm(em)). The enzyme activity is shown as the extinction increase/min. The $IC_{50}$ values listed in Table 2 are determined as those inhibitor concentrations which in each case led to a 50% inhibition of the enzyme.

The buffer solution contains 0.05% Brij (Sigma, Deisenhofen, Germany) and also 0.1 mol/L Tris/HCl, 0.1 mol/L NaCl, 0.01 mol/L $CaCl_2$ and 0.1 mol/L piperazine-N,N'-bis [2-ethanesulfonic acid] (pH=6.5). The enzyme solution contains 5 μg/ml of one of the enzyme domains prepared according to Ye et al. The substrate solution contains 1 mmol/L of the fluorogenic substrate (7-methoxycoumarin-4-yl)acetyl-Pro-Leu-Gly-Leu-3-(2',4'-dinitrophenyl)-L-2,3-diaminopropionyl-Ala-Arg-$NH_2$ (Bachem, Heidelberg, Germany).

TABLE 2

| Example No. | Stromelysin $IC_{50}$ (M) | Neutr. collagenase $IC_{50}$ (M) |
|---|---|---|
| 1 | $4 \times 10^{-7}$ | $1 \times 10^{-8}$ |
| 2 | $1 \times 10^{-7}$ | $9 \times 10^{-8}$ |
| 3 | $2 \times 10^{-5}$ | $2 \times 10^{-7}$ |
| 6 | $2 \times 10^{-7}$ | $2 \times 10^{-8}$ |
| 7 | $2 \times 10^{-7}$ | $4 \times 10^{-8}$ |
| 8 | $3 \times 10^{-7}$ | $1 \times 10^{-8}$ |
| 9 | $3 \times 10^{-7}$ | $2 \times 10^{-8}$ |
| 10 | $9 \times 10^{-8}$ | $1 \times 10^{-8}$ |
| 11 | $9 \times 10^{-8}$ | $3 \times 10^{-9}$ |
| 15 | $1 \times 10^{-7}$ | $1 \times 10^{-8}$ |
| 16 | $7 \times 10^{-8}$ | $7 \times 10^{-9}$ |
| 17 | $1 \times 10^{-7}$ | $2 \times 10^{-8}$ |
| 19 | $5 \times 10^{-7}$ | $5 \times 10^{-8}$ |
| 20 | $4 \times 10^{-7}$ | $2 \times 10^{-8}$ |
| 23 | $1 \times 10^{-6}$ | $6 \times 10^{-7}$ |
| 25 | $2 \times 10^{-7}$ | $4 \times 10^{-8}$ |
| 26 | $4 \times 10^{-7}$ | $4 \times 10^{-8}$ |
| 27 | $2 \times 10^{-7}$ | $1 \times 10^{-8}$ |
| 28 | $3 \times 10^{-7}$ | $6 \times 10^{-8}$ |
| 29 | $8 \times 10^{-8}$ | $9 \times 10^{-9}$ |
| 31 | $1 \times 10^{-6}$ | $5 \times 10^{-8}$ |
| 32 | $2 \times 10^{-7}$ | $4 \times 10^{-8}$ |
| 34 | $2 \times 10^{-7}$ | $2 \times 10^{-8}$ |
| 35 | $1 \times 10^{-7}$ | $1 \times 10^{-8}$ |
| 36 | $2 \times 10^{-7}$ | $1 \times 10^{-8}$ |
| 40 | $7 \times 10^{-8}$ | $2 \times 10^{-9}$ |
| 41 | $2 \times 10^{-7}$ | $3 \times 10^{-8}$ |
| 42 | $4 \times 10^{-7}$ | $3 \times 10^{-8}$ |
| 44 | $9 \times 10^{-8}$ | $1 \times 10^{-8}$ |
| 51 | $5 \times 10^{-8}$ | $5 \times 10^{-9}$ |
| 55 | $8 \times 10^{-7}$ | $4 \times 10^{-8}$ |
| 56 | $3 \times 10^{-8}$ | $5 \times 10^{-9}$ |
| 58 | $4 \times 10^{-8}$ | $6 \times 10^{-9}$ |
| 60 | $6 \times 10^{-7}$ | $2 \times 10^{-8}$ |
| 61 | $4 \times 10^{-7}$ | $2 \times 10^{-8}$ |
| 62 | $7 \times 10^{-9}$ | $2 \times 10^{-9}$ |
| 63 | $3 \times 10^{-6}$ | $6 \times 10^{-7}$ |
| 65 | $1 \times 10^{-7}$ | $3 \times 10^{-9}$ |
| 66 | $2 \times 10^{-8}$ | $2 \times 10^{-9}$ |
| 67 | $1 \times 10^{-6}$ | $2 \times 10^{-7}$ |
| 68 | $4 \times 10^{-7}$ | $1 \times 10^{-7}$ |
| 69 | $1 \times 10^{-8}$ | $4 \times 10^{-9}$ |
| 70 | $1 \times 10^{-7}$ | $3 \times 10^{-9}$ |
| 71 | $1 \times 10^{-8}$ | $2 \times 10^{-9}$ |
| 72 | $6 \times 10^{-7}$ | $2 \times 10^{-8}$ |
| 73 | $3 \times 10^{-7}$ | $2 \times 10^{-8}$ |
| 74 | $1 \times 10^{-7}$ | $1 \times 10^{-8}$ |
| 75 | $3 \times 10^{-7}$ | $2 \times 10^{-8}$ |
| 76 | $5 \times 10^{-9}$ | $3 \times 10^{-9}$ |
| 77 | $4 \times 10^{-9}$ | $4 \times 10^{-9}$ |

TABLE 2-continued

| Example No. | Stromelysin $IC_{50}$ (M) | Neutr. collagenase $IC_{50}$ (M) |
|---|---|---|
| 78 | $2 \times 10^{-8}$ | $2 \times 10^{-9}$ |
| 79 | $2 \times 10^{-8}$ | $4 \times 10^{-9}$ |
| 80 | $7 \times 10^{-9}$ | $2 \times 10^{-9}$ |
| 81 | $1 \times 10^{-8}$ | $2 \times 10^{-9}$ |
| 82 | $1 \times 10^{-7}$ | $1 \times 10^{-8}$ |
| 83 | $1 \times 10^{-6}$ | $2 \times 10^{-8}$ |
| 84 | $5 \times 10^{-6}$ | $2 \times 10^{-9}$ |
| 85 | $3 \times 10^{-6}$ | $3 \times 10^{-8}$ |
| 86 | $3 \times 10^{-7}$ | $1 \times 10^{-8}$ |
| 87 | $3 \times 10^{-8}$ | $5 \times 10^{-9}$ |
| 88 | $1 \times 10^{-7}$ | $7 \times 10^{-9}$ |
| 89 | $3 \times 10^{-7}$ | $2 \times 10^{-8}$ |
| 90 | $1 \times 10^{-8}$ | $2 \times 10^{-9}$ |
| 91 | $3 \times 10^{-7}$ | $1 \times 10^{-8}$ |
| 92 | $3 \times 10^{-8}$ | $4 \times 10^{-9}$ |
| 93 | $2 \times 10^{-7}$ | $2 \times 10^{-8}$ |
| 94 | $2 \times 10^{-7}$ | $3 \times 10^{-8}$ |
| 95 | $3 \times 10^{-7}$ | $2 \times 10^{-8}$ |
| 96 | $6 \times 10^{-7}$ | $2 \times 10^{-8}$ |
| 97 | $1 \times 10^{-6}$ | $3 \times 10^{-8}$ |
| 98 | $4 \times 10^{-7}$ | $3 \times 10^{-8}$ |
| 99 | $7 \times 10^{-7}$ | $5 \times 10^{-8}$ |
| 100 | $5 \times 10^{-7}$ | $2 \times 10^{-8}$ |
| 101 | $4 \times 10^{-8}$ | $4 \times 10^{-9}$ |
| 104 | $4 \times 10^{-8}$ | $5 \times 10^{-9}$ |
| 105 | $3 \times 10^{-8}$ | $1 \times 10^{-8}$ |
| 107 | $4 \times 10^{-8}$ | $1 \times 10^{-8}$ |

The present invention may be embodied in other specific forms without departing from its spirit or essential characteristics. The described embodiments are to be considered in all respects as illustrative only and not restrictive. The scope of the invention is, therefore, indicated by the appended claims rather than by the foregoing description. All changes which come within the meaning and range of equivalency of the claims are to be embraced within their scope.

What is claimed is:

1. A method of treating a disorder in the course of which an increased activity of a matrix-degrading metalloproteinase is obtained, the method comprising administering to a host in need thereof an efficacious amount of at least one compound of formula (I)

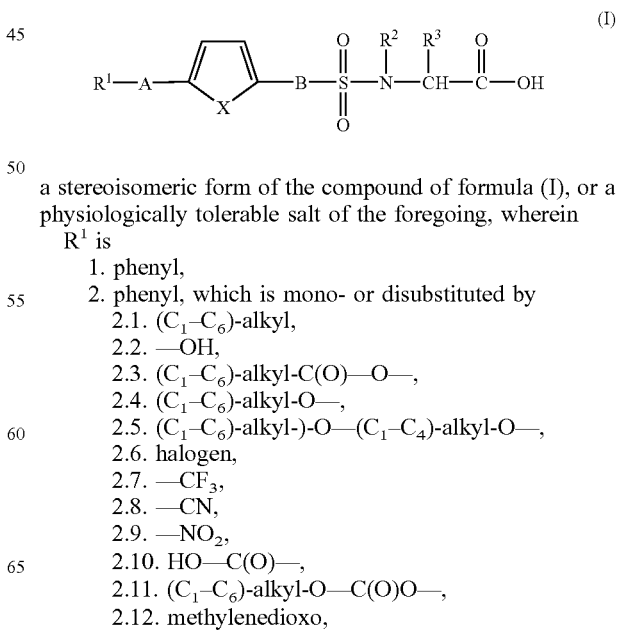

a stereoisomeric form of the compound of formula (I), or a physiologically tolerable salt of the foregoing, wherein
$R^1$ is
  1. phenyl,
  2. phenyl, which is mono- or disubstituted by
    2.1. ($C_1$–$C_6$)-alkyl,
    2.2. —OH,
    2.3. ($C_1$–$C_6$)-alkyl-C(O)—O—,
    2.4. ($C_1$–$C_6$)-alkyl-O—,
    2.5. ($C_1$–$C_6$)-alkyl-)-O—($C_1$–$C_4$)-alkyl-O—,
    2.6. halogen,
    2.7. —$CF_3$,
    2.8. —CN,
    2.9. —$NO_2$,
    2.10. HO—C(O)—,
    2.11. ($C_1$–$C_6$)-alkyl-O—C(O)O—,
    2.12. methylenedioxo, 2.13. $R^4$—$(R^5)$N—C(O)—, or 2.14. $R^4$—$(R^5)$N—;

$R^2$, $R^4$ and $R^5$ are identical or different, and each independently are 1. a hydrogen atom,
2. $(C_1$–$C_6)$-alkyl,
3. HO—C(O)—$(C_1$–$C_6)$-alkyl-,
4. phenyl-$(CH_2)$n-, in which phenyl is unsubstituted, or mono- or disubstituted by the radicals as defined under 2.1. to 2.14., and n is the integer zero, 1, or 2,
5. picolyl, or
6. $R^4$ and $R^5$ together with the ring amino group form a radical, wherein said radical has a 4- to 7 membered ring, in which one of the carbon atoms in said ring is optionally replaced by —O—, —S—, or —NH—, wherein said radical is at least one radical selected from azetidine, pyrrole, pyrroline, pyridine, azepine, piperidine, oxazole, isoxazole, imidazole, pyrazole, thiazole, isothiazole, diazepine, thiomorpholine, pyrimidine, and pyrazine;

$R^3$ is 1. a hydrogen atom,
2. $(C_1$–$C_{10})$-alkyl, in which alkyl is unsubstituted, or a hydrogen atom of the alkyl radical is replaced by —OH,
3. $(C_1$–$C_{10})$-alkenyl, in which alkenyl is linear or branched,
4. $R^2$—O—$(C_1$–$C_6)$-alkyl,
5. $R^2$—S(O)n-$(C_1$–$C_6)$-alkyl, where n has the above defined meaning,
6. $R^2$—S(O)(=NH)—$(C_1$–$C_6)$-alkyl-,
7.

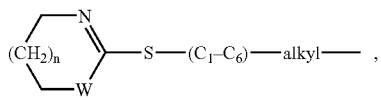

in which n is the integer zero, 1, or 2, and W is a nitrogen, oxygen, or sulfur atom, 8. phenyl-$(CH_2)_m$—, in which m is the integer zero, 1, 2, 3, 4, 5, or 6, —$(CH_2)_m$— is unsubstituted, or a hydrogen atom of —$(CH_2)_m$— is replaced by —OH, and phenyl is unsubstituted, or mono- or disubstituted by
   8.1. the radicals as described under 2.1. to 2.14.,
   8.2. —O—$(CH_2)_m$-phenyl, in which phenyl is unsubstituted, or mono- or disubstituted by the radicals as described under 2.1. to 2.14., and m is the integer zero, 1, 2, 3, 4, 5, or 6,
   8.3. —C(O)—$(CH_2)_m$-phenyl, in which phenyl is unsubstituted, or substituted as defined under 8.2.,
9. heteroaryl-$(CH_2)_m$—, in which heteroaryl is as defined under 9.1 to 9.15.;
   9.1. pyrrole,
   9.2. pyrazole,
   9.3. imidazole,
   9.4. triazole,
   9.5. thiophene,
   9.6. thiazole,
   9.7. oxazole,
   9.8. isoxazole,
   9.9. pyridine,
   9.10. pyrimidine,
   9.11. indole,
   9.12. benzothiophene,
   9.13. benzimidazole,
   9.14. benzoxazole, or
   9.15. benzothiazole;

m is defined above, —$(CH_2)_m$— is unsubstituted, or a hydrogen atom of —$(CH_2)_m$— is replaced by —OH, and heteroaryl is unsubstituted, or mono- or disubstituted by the radicals as described under 2.1. to 2.14., or $SO_2$-phenyl, in which phenyl is unsubstituted, or is substituted as defined under 8.2., or 10. $R^6$—C(O)—$(C_1$–$C_6)$-alkyl, in which $R^6$ is
    10.1. a hydrogen atom,
    10.2. $(C_1$–$C_6)$-alkyl,
    10.3. phenyl, in which phenyl is unsubstituted, or substituted by the radicals as defined under 2.1. to 2.14.,
    10.4. heteroaryl, in which heteroaryl is as defined under 9.1 to 9.15, and is unsubstituted, or is substituted by the radicals as defined under 2.1. to 2.14.,
    10.5. HO—,
    10.6. $R^{10}$O—, in which $R^{10}$ is
        10.6.1. $(C_1$–$C_6)$-alkyl,
        10.6.2. HO—C(O)—$(C_1$–$C_6)$-alkyl-,
        10.6.3. phenyl-$(CH_2)_n$—, in which phenyl is unsubstituted, or mono- or disubstituted by the radicals as defined under 2.1. to 2.14., and n is the integer zero, 1, or 2, or
        10.6.4. picolyl,
    10.7. $R^4$—$(R^5)$N, in which $R^4$ and $R^5$ are as defined above,
    10.8. heteroaryl-$(CH_2)_m$—NH—, in which heteroaryl is as defined under 9.0.1 to 9.0.15, is unsubstituted, or substituted by the radicals as defined under 2.1. to 2.14., and m is as defined above,
    10.9. $R^4$—$(R^5)$N—NH—, in which $R^4$ and $R^5$ are as defined above, or
    10.10. HO—C(O)—CH($R^3$)—NH—, in which $R^3$ is as defined above; or $R^2$ and $R^3$ together form a ring having a ring carboxyl group, of subformula (II)

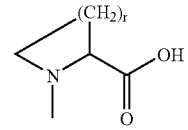

(II)

in which r is the integer 1, 2, or 3, the ring is unsubstituted, or one of the carbon atoms in the ring is replaced by —O—, or —S—, and the carbon atoms are unsubstituted, or are mono- or polysubstituted by $(C_1$–$C_6)$-alkyl, phenyl-, phenyl-$(CH_2)_m$—, or —OH; or in which r is the integer 1, 2, or 3, the ring is unsubstituted, or one of the carbon atoms in the ring is replaced by —$(R^7)$N—, in which $R^7$ is 1. a hydrogen atom,
2. $(C_1$–$C_6)$-alkyl,
3. phenyl, in which phenyl is unsubstituted, or is substituted by the radicals as defined under 2.1. to 2.14., or 4. benzyl, in which benzyl is unsubstituted, or is substituted by the radicals as defined under 2.1. to 2.14., or
5. $R^2N-C(=NH)-$, where $R^2$ has the above defined meaning, and the other carbon atoms in the ring of subformula (II) are unsubstituted, or mono- or polysubstituted by $(C_1-C_6)$-alkyl-, phenyl-, phenyl-$(CH_2)_m-$, or $-OH$;

A is
a) a covalent bond,
b) $-O-$,
c) $-CH=CH-$ or
d) $-C\equiv C-$;

B is
a) $-(CH_2)_m-$, in which m is as defined above,
b) $-O-(CH_2)_p-$, in which p is an integer 1, 2, 3, 4, or 5, or
c) $-CH=CH-$; and X is a sulfur atom,
wherein the disorder is a collagenose, immunologically or metabolically related acute or chronic arthritide, or arthropathy.

2. A method of treating a disorder in the course of which an increased activity of a matrix-degrading metalloproteinase is obtained, the method comprising administering to a host in need thereof an efficacious amount of at least one compound of formula (VI)

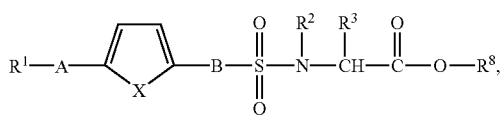

(VI)

a stereoisomeric form thereof, or a physiologically tolerable salt of the foregoing, wherein $R^1$ is
1. phenyl,
2. phenyl, which is mono- or disubstituted by
   2.1. $(C_1-C_6)$-alkyl,
   2.2. $-OH$,
   2.3. $(C_1-C_6)$-alkyl-C(O)$-O-$,
   2.4. $(C_1-C_6)$-alkyl-O$-$,
   2.5. $(C_1-C_6)$-alkyl-O$-(C_1-C_4)$-alkyl-O$-$,
   2.6. halogen,
   2.7. $-CF_3$,
   2.8. $-CN$,
   2.9. $-NO_2$,
   2.10. HO$-$C(O)$-$,
   2.11. $(C_1-C_6)$-alkyl-O$-$C(O)O$-$,
   2.12. methylenedioxo,
   2.13. $R^4-(R^5)N-C(O)-$, or
   2.14. $R^4-(R^5)N-$, or $R^2$, $R^4$ and $R^5$ are identical or different, and each independently are
1. a hydrogen atom,
2. $(C_1-C_6)$-alkyl,
3. HO$-$C(O)$-(C_1-C_6)$-alkyl,
4. phenyl-$(CH_2)_n-$, in which phenyl is unsubstituted, or mono- or disubstituted by the radicals as defined under 2.1. to 2.14., and n is the integer zero, 1, or 2, or
5. picolyl, or 6. $R^4$ and $R^5$ together with the ring amino group form a radical, wherein said radical has a 4- to 7 membered ring, in which one of the carbon atoms in said ring is optionally replaced by $-O-$, $-S-$, or $-NH-$, wherein said radical is at least one radical selected from azetidine, pyrrole, pyrroline, pyridine, azepine, piperidine, oxazole, isoxazole, imidazole, pyrazole, thiazole, isothiazole, diazepine, thiomorpholine, pyrimidine, and pyrazine;

$R^3$ is
1. a hydrogen atom,
2. $(C_1-C_{10})$-alkyl, in which alkyl is unsubstituted, or a hydrogen atom of the alkyl radical is replaced by $-OH$,
3. $(C_1-C_{10})$-alkenyl, in which alkenyl is linear or branched,
4. $R^2-O-(C_1-C_6)$-alkyl,
5. $R^2-S(O)_n-(C_1-C_6)$-alkyl, where n has the above defined meaning,
6. $R^2-S(O)(=NH)-(C_1-C_6)$-alkyl,
7.

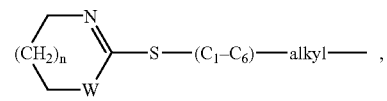

in which n is the integer zero, 1, or 2, and W is a nitrogen, oxygen, or sulfur atom,
8. phenyl-$(CH_2)_m-$, in which m is the integer zero, 1, 2, 3, 4, 5, or 6, $-(CH_2)_m-$ is unsubstituted, or a hydrogen atom of $-(CH_2)_m-$ is replaced by $-OH$, and phenyl is unsubstituted, or mono- or disubstituted by
   8.1. the radicals as described under 2.1. to 2.14.,
   8.2. $-O-(CH_2)_m$-phenyl, in which phenyl is unsubstituted, or mono- or disubstituted by the radicals as described under 2.1. to 2.14., and m is the integer zero, 1, 2, 3, 4, 5, or 6,
   8.3. $-C(O)-(CH_2)_m$-phenyl, in which phenyl is substituted as defined under 8.2.,
9. heteroaryl-$(CH_2)_m-$, in which heteroaryl is as defined under 9.1 to 9.15.;
   9.1. pyrrole,
   9.2. pyrazole,
   9.3. imidazole,
   9.4. triazole,
   9.5. thiophene,
   9.6. thiazole,
   9.7. oxazole,
   9.8. isoxazole,
   9.9. pyridine,
   9.10. pyrimidine,
   9.11. indole,
   9.12. benzothiophene,
   9.13. benzimidazole,
   9.14. benzoxazole, or
   9.15. benzothiazole;

m is defined above, $-(CH_2)_m-$ is unsubstituted, or a hydrogen atom of $-(CH_2)_m-$ is replaced by $-OH$, and heteroaryl is unsubstituted, or mono- or disubstituted by the radicals as described under 2.1. to 2.14., or $-SO_2$-phenyl, in which phenyl is unsubstituted, or is substituted as defined under 8.2., or 10. $R^6$—C(O)—($C_1$–$C_6$)-alkyl, in which $R^6$ is
   10.1. a hydrogen atom,
   10.2. ($C_1$–$C_6$)-alkyl,
   10.3. phenyl, in which phenyl is unsubstituted, or substituted by the radicals as defined under 2.1. to 2.14.,
   10.4. heteroaryl, in which heteroaryl is as defined under 9.1 to 9.15, and is unsubstituted, or is substituted by the radicals as defined under 2.1. to 2.14.,
   10.5. HO—,
   10.6. $R^{10}$O—, in which $R^{10}$ is
      10.6.1. ($C_1$–$C_6$)-alkyl,
      10.6.2. HO—C(O)—($C_1$–$C_6$)-alkyl-,
      10.6.3. phenyl-$(CH_2)_n$—, in which phenyl is unsubstituted, or mono- or disubstituted by the radicals as defined under 2.1. to 2.14., and n is the integer zero, 1, or 2, or
      10.6.4. picolyl,
   10.7. $R^4$—($R^5$)N, in which $R^4$ and $R^5$ are as defined above,
   10.8. heteroaryl-$(CH_2)_m$—NH—, in which heteroaryl is as defined under 9.0.1 to 9.0.15, is unsubstituted, or substituted by the radicals as defined under 2.1. to 2.14., and m is as defined above,
   10.9. $R^4$—($R^5$)N—NH—, in which $R^4$ and $R^5$ are as defined above, or
   10.10. HO—C(O)—CH($R^3$)—NH—, in which $R^3$ is as defined above; or
$R^2$ and $R^3$ together form a ring having a ring carboxyl group, of subformula (II)

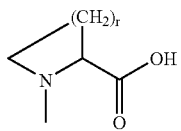

(II)

in which r is the integer 1, 2, or 3, the ring is unsubstituted, or one of the carbon atoms in the ring is replaced by —O—, —S—, or —($R^7$)N—, in which $R^7$ is
1. a hydrogen atom,
2. ($C_1$–$C_6$)-alkyl,
3. phenyl, in which phenyl is unsubstituted, or is substituted by the radicals as defined under 2.1. to 2.14., or
4. benzyl, in which benzyl is unsubstituted, or is substituted by the radicals as defined under 2.1. to 2.14., or
5. $R^2$N—C(=NH)—, where $R^2$ has the above defined meaning; and/or the other carbon atoms in the ring of subformula (II) are mono- or polysubstituted by ($C_1$–$C_6$)-alkyl-, phenyl-, phenyl-$(CH_2)_m$—, or —OH;

A is
   a) a covalent bond,
   b) —O—,
   c) —CH=CH— or
   d) —C≡C—;

B is
   a) —$(CH_2)_m$—, in which m has the above defined meaning,
   b) —O—$(CH_2)_p$—, in which p is an integer 1, 2, 3, 4, or 5, or
   c) —CH=CH—;

X is a sulfur atom,
$R^8$ is a hydrogen atom, ($C_1$–$C_6$)-alkyl, phenyl, or benzyl,
wherein the disorder is a collagenose, immunologically or metabolically related acute or chronic arthritide, or arthropathy.

* * * * *